(12) United States Patent
Benedini et al.

(10) Patent No.: US 6,613,784 B1
(45) Date of Patent: Sep. 2, 2003

(54) NITROXYDERIVATIVES HAVING ANTINFLAMMATORY, ANALGESIC AND ANTITHROMBOTIC ACTIVITY

(75) Inventors: Francesca Benedini, Milan (IT); Piero Del Soldato, Monza (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/926,095

(22) PCT Filed: Feb. 23, 2000

(86) PCT No.: PCT/EP00/01454

§ 371 (c)(1),
(2), (4) Date: Aug. 30, 2001

(87) PCT Pub. No.: WO00/51988

PCT Pub. Date: Sep. 8, 2000

(30) Foreign Application Priority Data

Mar. 2, 1999 (IT) .......................................... MI99A0413

(51) Int. Cl.$^7$ ...................... C07D 213/30; A61K 31/44
(52) U.S. Cl. ...................... 514/357; 546/334; 546/335
(58) Field of Search .................. 546/334, 335; 514/357

(56) References Cited

U.S. PATENT DOCUMENTS

| | | | |
|---|---|---|---|
| 2,396,145 A | 3/1946 | Askelof et al. ............. 260/156 |
| 2,998,450 A | 8/1961 | Wilbert et al. ............. 260/562 |
| 3,161,654 A | 12/1964 | Shen ........................ 260/319 |
| 3,228,831 A | 1/1966 | Nicholson et al. ........... 167/53 |
| 3,337,570 A | 8/1967 | Sherlock et al. ......... 260/295.5 |
| 3,558,690 A | 1/1971 | Sallmann et al. ........... 260/471 |
| 3,591,584 A | 7/1971 | Lombardino ................ 260/243 |
| 3,600,437 A | 8/1971 | Marshall .................... 260/520 |
| 3,641,127 A | 2/1972 | Farge et al. ................. 260/516 |
| 3,652,589 A | 3/1972 | Flick et al. .............. 260/326.5 |
| 3,689,653 A | 9/1972 | Sherlock et al. ............. 424/266 |
| 3,755,427 A | 8/1973 | Adams et al. ............... 260/515 |
| 3,784,701 A | 1/1974 | Tomcufcik et al. ......... 424/317 |
| 3,843,681 A | 10/1974 | Demerson et al. ..... 260/326.1 |
| 3,896,145 A | 7/1975 | Berger et al. ............... 260/315 |
| 3,904,682 A | 9/1975 | Fried et al. ................. 260/520 |
| 3,931,205 A | 1/1976 | Nakanishi et al. .......... 260/295 |
| 3,997,669 A | 12/1976 | Carney et al. .............. 424/274 |
| 4,035,376 A | 7/1977 | Janssen et al. ............. 260/295 |
| 4,061,779 A | 12/1977 | Lake et al. ................. 424/331 |
| 4,089,969 A | 5/1978 | Muchowski et al. ........ 424/274 |
| 4,161,538 A | 7/1979 | Terada et al. ............... 424/317 |
| 4,238,620 A | 12/1980 | Uno et al. ..................... 549/13 |
| 4,254,274 A | 3/1981 | Terada et al. ................. 560/51 |
| 4,528,367 A | 7/1985 | Agback et al. ............. 534/599 |
| 4,556,672 A | 12/1985 | Kadin ........................ 514/414 |
| 5,861,426 A | 1/1999 | Del Soldato et al. ........ 514/413 |

FOREIGN PATENT DOCUMENTS

| | | |
|---|---|---|
| DE | 25 37 070 | 3/1976 |
| DE | 27 56 113 | 6/1979 |
| EP | 0 026 928 | 4/1981 |
| EP | 0 036 636 | 9/1981 |
| EP | 0 054 812 | 6/1982 |
| EP | 0 147 177 | 7/1985 |
| EP | 0 238 226 | 9/1987 |
| FR | 1574570 | 7/1989 |
| GB | 2 003 877 A | 3/1979 |
| GB | 2 035 311 A | 6/1990 |
| GB | 2 283 238 A | 5/1995 |
| WO | WO 92/01668 | 2/1992 |
| WO | WO 94/04484 | 3/1994 |
| WO | WO 95/30641 | 11/1995 |
| WO | WO 95/30641 A | * 11/1995 |
| WO | WO 97/16405 A | * 5/1997 |

OTHER PUBLICATIONS

Vane et al.; FASEB J. vol. 1, pp. 89–96 (1987) "Inflammation and the mechanism of action of anti–inflammatory drugs".

Smith et al.; Biochimica et Biophysica Acta, 1083, pp. 1–17 (1991); "Prostaglandin endoperoxide syhthase: structure and catalysis".

The Merck Index, An Encyclopedia of Chemicals, Drugs and Biologicals, XI Ed., 1989, p. 16, No. 95.

Yalkowsky et al.; J. Pharmaceutical Sciences, vol. 72, No. 9, pp. 1014–1017 (Sep. 1983), "In Vitro Method for Detecting Precipitation of Parenteral Formulations After Injection".

H. Weil; Über die Reduktion substituierter Salicylsäuren, Ber. 55B, 2664 (1922).

Walsh et al.; J. Medicinal Chemistry, vol. 27, No. 11, pp. 1379–1388 (Nov. 1984); "Antiinflammatory Agents. 3. Synthesis and Pharmacological Evaluation of 2–Amino–3–benzoylphenylacetic Acid and Analogues".

* cited by examiner

Primary Examiner—Zinna Northington Davis
(74) Attorney, Agent, or Firm—Arent Fox Kintner Plotkin & Kahn PLLC

(57) ABSTRACT

Organic or inorganic salts of compounds of general formula: A—X$_1$—N(O)$_z$ for use as medicaments having anti-inflammatory, analgesic and antithrombotic activity, wherein A is R(COX$_u$)$_t$ wherein t is 0 or 1; u is 0 or 1 and X is O, NH, NR$_{1c}$ wherein R$_{1c}$ us a C$_1$–C$_{10}$ alkyl and R is, for example, (Ia) wherein R$_1$ is acetoxy, preferably in ortho position with respect to —CO— and R$_2$ is hydrogen or acetylsalicylsalicylic acid derivatives; and X$_1$ is the formula (B), Y being a ring containing at least one salified nitrogen atom.

12 Claims, No Drawings

NITROXYDERIVATIVES HAVING ANTINFLAMMATORY, ANALGESIC AND ANTITHROMBOTIC ACTIVITY

The present invention relates to new products having anti-inflammatory, analgesic and antithrombotic activity.

Specifically it relates to cyclo-oxygenase (COX) inhibitors.

It is known that the anti-inflammatory and antithrombotic efficacy of NSAIDs (Non steroid antiinflammatory drugs), also known as FANS (non steroid antiinflammatory drugs), but esoecially their tolerability, seem to be considerably affected by their inhibitory activity of the cyclo-oxygenase (COX) both in the inflammatory site and in the healthy tissue. See for example FASEB Journal 1, 89, 1987; Bioch. Biophys. Acta 1083, 1, 1991. The drawback of these products is that they are toxic, as already described in U.S. Pat. No. 5,861,426.

Nitroderivative compounds, described in said patent, are also known, have an high efficacy in the cyclooxygenase inhibition and a low toxicity. However these compounds show some drawbacks connected to the chemical-physical and structural characteristics of the molecules themselves, these latter being highly lipophilic and therefore having a poor solubility in water. It is well known that the solubilization process is decisive for absorption and interaction with the effector. The poor solubility generally involves a variable and unpredictable efficacy whereby it is difficult to set a correct posology. In practice it is necessary to administer higher doses in order to contain the above mentioned variabilities. The drawback is the risks of a higher incidence of side effects. Another disadvantage bound to the poor solubility of the nitroderivatives of said patent application is that they are difficult to be formulated. It is well known that the solubility in water of a molecule is one of the most important properties affecting the pharmacokinetic and pharmacodynamic processes. For example for parenteral administration, particularly by intravenous route, drugs must be formulated in solutions. In order to increase solubility, when it is unsatisfactory for these uses, the choice of suitable solvents and/or excipients is therefore critical, for example, among the latter, surfactants, etc., can be mentioned. This can lead to drawbacks from the toxicological point of view connected to the excipient tolerability; besides there are other drawbacks for example in the intravenous formulation which, as well known, must not cause haemolysis or incompatibility with blood constituents. Besides it is necessary to notice that it is well known that surfactants and apolar solvents can be irritant. See for example J. Pharm. Science 72, 1014, 1983.

Experiments carried out by the Applicant, wherein 0.1% Tween 80 and 1% dimethylsulphoxide have been used to suspend the nitroxy derivatives of the antiinflammatory compounds described in the patent application WO 95/30641 have shown that these substances were irritant towards the gastric mucous membrane.

It has unexpectedly been found that the derivatives of the present invention, differently from the above mentioned compounds of the prior art, can be solubilized without using the substances commonly used in the pharmaceutical technique to obtain solutions or suspensions, maintaining or even improving the activity of the prior art nitroxy derivatives. A further advantage of the compounds of the present invention is that it is possible to avoid adding to the formulation the excipients, such as for example those above mentioned, which cause or can induce irritant effects.

The antiinflammatory products described in the present application have an high cyclo-oxygenase inhibiting activity combined with low toxicity and pharmacokinetic good responses, and have furthermore a better systemic absorption degree.

This is quite surprising and unexpected since the factors affecting the FANS antiinflammatory and antithrombotic efficacy depend on various parameters whereby it is not possible to foresee a priori the pharmacokinetics, for example the absorbed product fraction, the pharmacodynamic activity, the toxicity and the COX inhibiting properties and most of all, no assumptions can be made to predict or limit the response variability.

An object of the present invention are compounds or organic or inorganic salts of compounds of general formula:

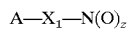

for use as medicaments, specifically as antiinflammatory and antithrombotic agents, wherein:

z is an integer and is 1 or 2, preferably 2;

$A = R(COX_u)_t$ and wherein t is an integer 0 or 1; u is 0 or 1;

X=O, NH, $NR_{1c}$ wherein $R_{1c}$ is a linear or branched $C_1$–$C_{10}$ alkyl;

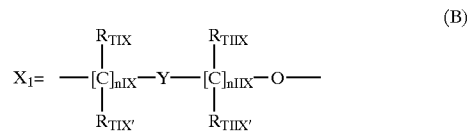

(B)

wherein:

nIX is an integer between 0 and 3, preferably 1;

nIIX is an integer between 1 and 3, preferably 1;

$R_{TIX}$, $R_{TIX'}$, $R_{TIIX}$, $R_{TIIX'}$, equal to or different from each other, are H or linear or branched $C_1$–$C_4$ alkyl; preferably $R_{TIX}$, $R_{TIX'}$, $R_{TIIX}$, $R_{TIIX'}$ are H;

Y is a ring containing at least one salifiable nitrogen atom;

preferably Y is an heterocyclic ring, saturated or unsaturated or aromatic, having preferably 5 or 6 atoms and containing at least one or two nitrogen atoms, preferably one or two nitrogen atoms;

R is selected from the following groups:

Group I) wherein t=1 and u=1

Ia)

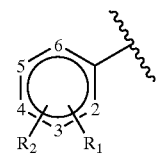

Ib)

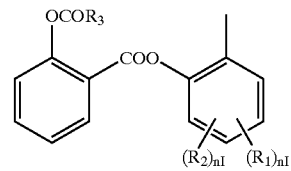

Ic)
-continued

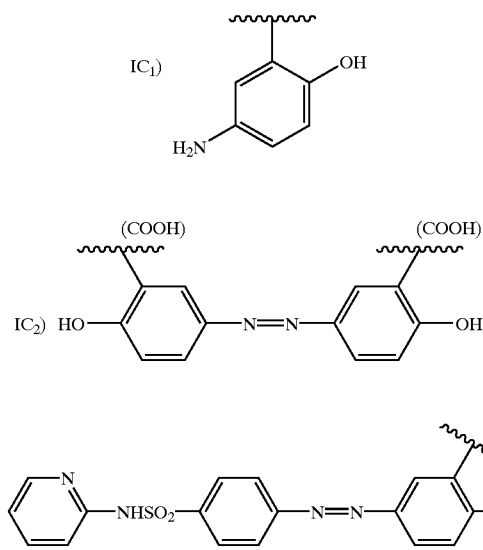

wherein:
R₁ is the OCOR₃ group; wherein R₃ is methyl, ethyl or linear or branched $C_3$–$C_5$ alkyl, or the residue of a heterocycle with a single ring having 5 or 6 atoms which may be aromatic, partially or totally hydrogenated, containing one or more hetero-atoms independently selected from O, N and S;
R₂ is hydrogen, hydroxy, halogen, a linear or when possible branched $C_1$–$C_4$ alkyl, a linear or when possible branched $C_1$–$C_4$ alkoxyl; a linear or when possible branched $C_1$–$C_4$ perfluoroalkyl, for example trifluoromethyl; nitro, amino, mono- or di- ($C_{1-4}$) alkylamino;
nI is an integer 0 or 1;

Preferably in the Compounds of Formula Ia) X is Equal to O or NH, R₁ is acetoxy, preferably in ortho position with respect to —CO—, R₂ is hydrogen; in $X_1 R_{TIX}=R_{TIX}=R_{TIIX}=R_{TIIX}$ H, $n_{IX}=n_{IIX}=1$ and Y is an aromatic ring having 6 atoms, containing one nitrogen atom, said aromatic ring having the two free valences in position 2 and 6.

Preferably in the Compounds of Formula Ib) $R_3=CH_3$, nI=0, X is equal to O, X₁ is as above defined for Ia); in this case Ib) is the residue of the acetylsalicylsalicylic acid.

The compounds Ic) of formula Ic₁) are the 5-amino salicylic acid derivatives (5-amino-2-hydroxybenzoic acid), for example mesalamine, when the valence is saturated with —COOH.

In the compounds of formula Ic₂) at least one of the two carboxyl groups is reacted for obtaining the invention compounds. When both carboxyl groups react, bifunctional compounds are obtained. When the two valences are saturated with —COOH, the compound known as olsalazine is obtained. When one of the two valences instead of —COOH is saturated with —CONHCH₂—CH₂—COOH, the compound is known as balsalazide, wherein —OH which is in ortho position in the same aromatic ring is substituted with H.

The compounds of formula IC₃) are known as sulphalazine: 2-hydroxy-5-[(2-pyridinylamino)sulphonyl]phenyl]azo] benzoic acid when the free valence is saturated with —COOH.

The preferred Ic) compounds have X=O and u=1;

Group II) wherein t=1, u=1

IIa)

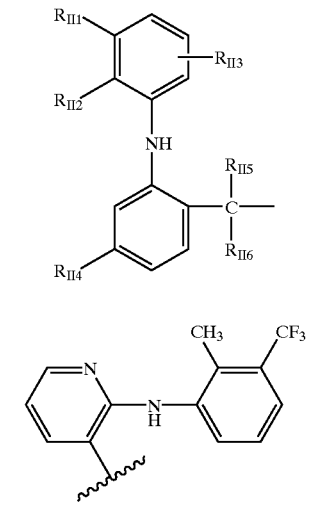

IIb)

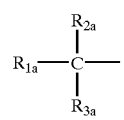

wherein:
$R_{II5}$ is H, a linear or branched when possible $C_1$–$C_3$ alkyl;
$R_{II6}$ has the same meaning as $R_{II5}$, or when $R_{II5}$ is H it may be benzyl;
$R_{II1}$, $R_{II2}$ and $R_{II3}$ can independently be hydrogen, a linear or when possible branched $C_1$–$C_6$ alkyl or a linear or when possible branched $C_1$–$C_6$ alkoxy, or Cl, F, Br;
$R_{II4}$ is $R_{II1}$ or bromine;
the compounds wherein $R_{II1}$, $R_{II4}$ are hydrogen and $R_{II2}$ and $R_{II3}$ are chlorine in ortho position with respect to NH are preferred;
$R_{II5}$ and $R_{II6}$ are H, X is equal to O, and X₁ is as above defined for the compounds of formula Ia);
IIb) is the residue of the 2-[(2-methyl-3-(trifluoromethyl)phenyl]amino]-3-pyridincarboxylic] acid and when the —COOH group is present the compound is known as flunixin;
Group III) wherein t=1, u=1 and R is

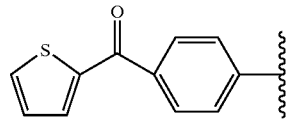

wherein:
$R_{2a}$ and $R_{3a}$ are H, a linear or when possible branched, $C_1$–$C_{12}$ alkyl or allyl, with the proviso that when one of the two is allyl, the other is H;
preferably $R_{2a}$ is H, $C_1$–$C_4$ alkyl, $R_{3a}$ is H;
$R_{1a}$ is selected from (II)

-continued
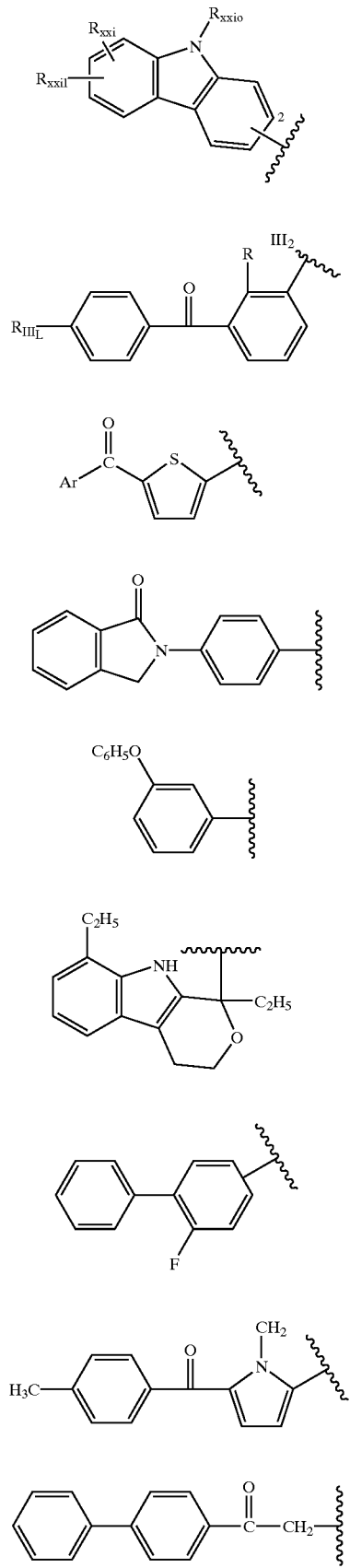
IIID) $R_{1a}$ corresponds to the following formulas:
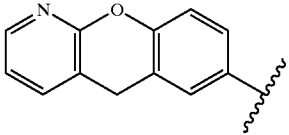
(IIIa)
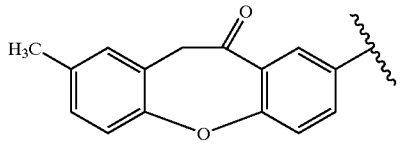
(XXX)
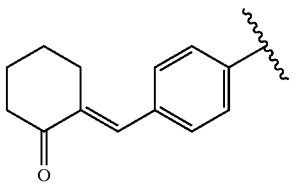
(XXXI)
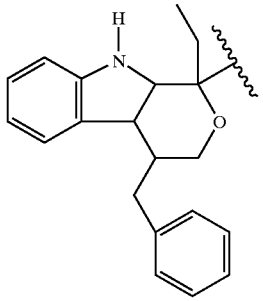
(XXXII)
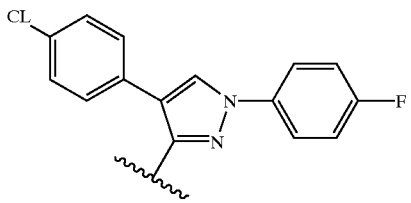
(XXXIII)
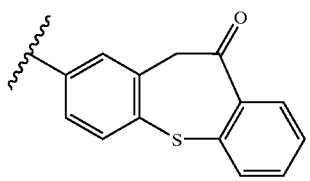
(XXXVI)
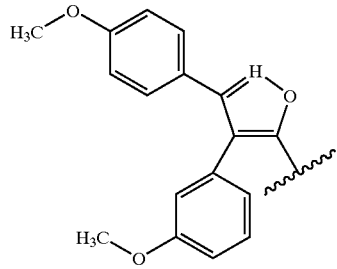
(XXXVII)
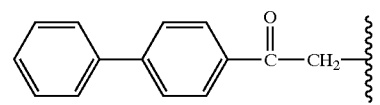

-continued

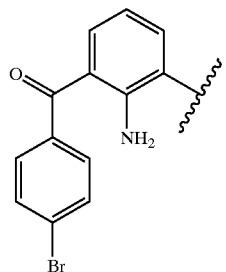

(XII)

wherein the meanings are the following:
when $R_{1a}$ is as defined in formula (IV), Ketoprofen residue:
  $R_{III1}$ is H,
  $R_{III2}$ is H, hydroxy;
  preferred are the compounds wherein $R_{III1}$ and $R_{III2}$ are H,
  $R_{3a}$ is H, and $R_{2a}$ is methyl, X=O;
when $R_{1a}$ is as defined in formula (XXI), carprofen residue:
  $R_{xxio}$ is H, a linear or when possible branched alkyl having from 1 to 6 C atoms, a $C_1-C_6$ alkoxycarbonyl bound to a $C_1-C_6$ alkyl, $C_1-C_6$ carboxyalkyl, $C_1-C_6$ alkanoyl, optionally substituted with halogens, benzyl or halobenzyl, benzoyl or halobenzoyl;
  $R_{xxi}$ is H, halogen, hydroxy, CN, $C_1-C_6$ alkyl optionally containing OH groups, $C_1-C_6$ alkoxy, acetyl, benzyloxy, $SR_{xxi2}$ wherein $R_{xxi2}$ is $C_1-C_6$ alkyl; $C_1-C_3$ perfluoroalkyl; $C_1-C_6$ carboxyalkyl optionally containing OH groups, $NO_2$, amino; sulphamoyl, di-alkyl sulphamoyl with $C_1-C_6$ alkyl, or difluoroalkylsulphonyl with $C_1-C_3$ alkyl;
  $R_{xxi1}$ is halogen, CN, $C_1-C_6$ alkyl containing one or more OH groups, $C_1-C_6$ alkoxy, acetyl, acetamido, benzyloxy, $SR_{III3}$ being $R_{III3}$ as above defined, $C_1-C_3$, perfluoroalkyl, hydroxy, $C_1-C_6$ carboxyalkyl, $NO_2$, amino, mono- or di-alkylamino $C_1-C_6$; sulphamoyl, di-alkyl sulphamoyl $C_1-C_6$, or di-fluoroalkyklsulphamoyl as above defined; or $R_{xxi}$ together with $R_{xxi1}$ is a $C_1-C_6$ alkylene dioxy;
  preferred are the compounds wherein $R_{xxio}$ is H, the linking bridge is in position 2, $R_{xxi}$ is H, $R_{xxi1}$ is chlorine and is in para position with respect to nitrogen;
  $R_{3a}$ is H, $R_{2a}$ is methyl and X is O;
when $R_{1a}$ is as defined in the formula (XXXV), residue of the tiaprofenic acid:
  Ar is phenyl, hydroxyphenyl optionally mono- or poly-substituted with halogen, alkanoyl and $C_1-C_6$ alkoxy, $C_1-C_6$ trialkyl, preferably $C_1-C_3$, cyclopentyl, cyclohexyl cycloheptyl, thienyl, furyl optionally containing OH, pyridyl;
  the preferred compounds of (XXXV) are those wherein Ar is phenyl, $R_{3a}$ is H, $R_{2a}$ is methyl and X is O;
when $R_{1a}$ is as defined in formula (II), suprofen residue, of which the preferred one has been shown, wherein $R_{3a}$ is H, $R_{2a}$ is methyl and X=O, as described and obtained in U.S. Pat. No. 4,035,376 herein incorporated by reference;

when $R_{1a}$ is as defined in formula (VI), R is the residue of indoprofen when $R_{2a}$=H and $R_3$a=$CH_3$;
  of indobufen when $R_{2a}$ is equal to H and $R_{3a}$=$C_2H_5$;
  X=O, as described and obtained according to U.S. Pat. No. 3,997,669 herein incorporated by reference;
when $R_{1a}$ is as defined in formula (VIII), R is the residue of etodolac when $R_{2a}$=$R_{3a}$=H and X=O, as described in and obtained according to U.S. Pat. No. 3,843,681 herein incorporated by reference;
when $R_{1a}$ is as defined in formula (VII), R is the residue of fenoprofen when $R_{3a}$=H, $R_{2a}$=$CH_3$ and X=O, as described and obtained according to U.S. Pat. No. 3,600,437 herein incorporated by reference;
when $R_{1a}$ is as defined in formula (III), R is the residue of fenbufen when $R_{2a}$=$R_{3a}$=H and X=O, as described and obtained according to U.S. Pat. No. 3,784,701 herein incorporated by reference;
when $R_{1a}$ is as defined in formula (IX), R is the residue of flurbiprofen when $R_{3a}$=H, $R_{2a}$=$CH_3$, X=O;
when $R_{1a}$ is as defined in formula (X) R is the residue of tolmetin when $R_{2a}$=$R_{3a}$=H, X=O, as described in and obtained according to FR 1,574,570 herein incorporated by reference.

In the group IIID) $R_{1a}$ corresponds to the following formulas:
  IIIa), when $R_{2a}$=H and $R_{3a}$=$CH_3$ the residue of pranoprofen is obtained: α-methyl-5H-[1]benzopyrano-[2,3-b]pyridin-7-acetic acid; in the preferred compound $R_{2a}$=H, $R_{3a}$=$CH_3$, u=1 and X=O:
  (XXX), when $R_{2a}$=H and $R_{3a}$=$CH_3$ the bermoprofen residue is obtained: dibenz[b,f]oxepin-2-acetic acid; in the preferred compound $R_{2a}$=H, $R_{3a}$=$CH_3$, u=1 and X=O.
  (XXXI), when $R_{2a}$=H and $R_{3a}$=$CH_3$, R is the radical of the compound CS-670: 2-[4-(2-oxo-1-cyclohexylidene methyl) phenyl]propionic acid; the preferred compound has $R_{2a}$=H, $R_{3a}$=$CH_3$, u=1 and X=O;
  (XXXII), when $R_{2a}$=$R_{3a}$=H the Pemedolac residue is obtained; the preferred compound has $R_{2a}$=$R_{3a}$=H, u=1 and X=O;
  (XXXIII), when $R_{2a}$=$R_{3a}$=H the pirazolac residue is obtained: derivatives of the 4-(4-chlorophenyl)-1-(4-fluorophenyl)-3-pyrazolic acid; the preferred compounds have $R_{2a}$=$R_{3a}$=H, u=1 and X=O.
  (XXXVI), when $R_{2a}$=H, $R_{3a}$=$CH_3$, the zaltoprofen residue is obtained; when the residue is saturated with an hydroxyl or aminic group, or with the carboxylic function the compounds are known as dibenzothiepin derivatives; in the preferred compounds $R_{2a}$=H, $R_{3a}$=CH, u=1 and X=O.
  (XXXVII), when $R_{2a}$=$R_{3a}$=H the mofezolac residue is obtained: 3,4-di(p-methoxyphenyl)isoxazol-5-acetic acid when the residue is $CH_2$—COOH; in the preferred compounds $R_{2a}$=$R_{3a}$=H, t=1 and X=O;
  (XII), when $R_{2a}$=$R_{3a}$=H the bromfenac residue is obtained: 2-amino-3-(4-bromobenzoyl)benzeneacetic acid; the preferred compounds have u=1, t=1, X=O, $R_{2a}$=$R_{3a}$=H; or t=0;

In the group IV) wherein t=1, u=1, R is

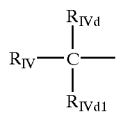

wherein:
$R_{IVd}$ and $R_{IVd1}$ are at least one H and the other a linear or branched when possible alkyl from $C_1$ to $C_6$, preferably $C_1$ and $C_2$, or difluoroalkyl with the alkyl having from 1 to 6 C atoms, $C_1$ is preferred, or $R_{IVd}$ and $R_{IVd1}$ form together a methylene group;
$R_{IV}$ has the following meaning:

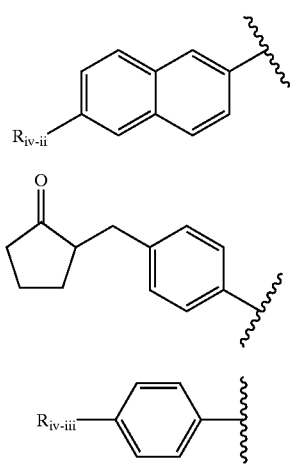

(II)

(XB)

(IIIB)

wherein the compounds of group IV) have the following meanings: in formula (IIB)
$R_{iv-ii}$ is $C_1-C_6$ alkyl, $C_3-C_7$ cycloalkyl, $C_1-C_7$ alkoxymethyl, $C_1-C_3$ trifluoroalkyl, vinyl, ethynyl, halogen, $C_1-C_6$ alkoxy, difluoroalkoxy, with the $C_1-C_7$ alkyl, $C_1-C_7$ alkoxymethyloxy, alkylthiomethyloxy with the $C_1-C_7$ alkyl, alkyl methylthio with the $C_1-C_7$ alkyl, cyano, difluoromethylthio, phenyl- or phenylalkyl substituted with the $C_1-C_8$ alkyl; preferably $R_{iv-ii}$ is $CH_3O-$, $R_{IVd}$ is H and $R_{IVd1}$ is $CH_3$, and is known as naproxen residue;
X=O and $X_1$ is as above defined for Ia);
in formula (X B), of which the loxoprofen residue has been shown, described in U.S. Pat. No. 4,161,538 the compounds are preferred wherein $R_{IVd}$ is H and $R_{IVd1}$ is $CH_3$, X=O and $X_1$ is as above defined for Ia);
in formula (IIIB):
$R_{iv-iii}$ is a $C_2-C_5$ alkyl, optionally branched when possiblle, $C_2$ and $C_3$ alkyloxy, allyloxy, phenoxy, phenylthio, cycloalkyl from 5 to 7 C atoms, optionally substituted in position 1 with a $C_1-C_2$ alkyl;
the compound in which $R_{iv-iii}$ is

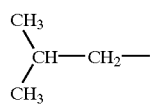

and $R_{IVd}$=H, $R_{IVd1}$ is $CH_3$, is preferred, a compound known as ibuprofen residue; X=O and $X_1$ is as above defined for Ia);

Group V)

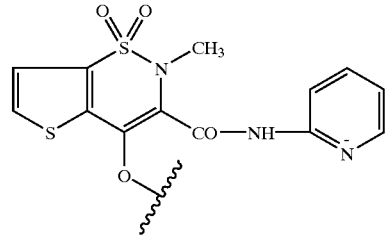

(VIIC)

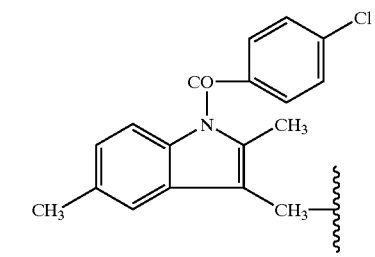

(IXC)

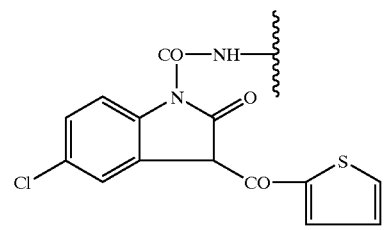

(IVC)

(V)

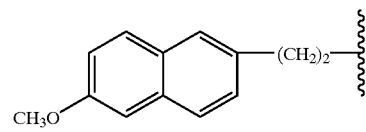

(IIIC)

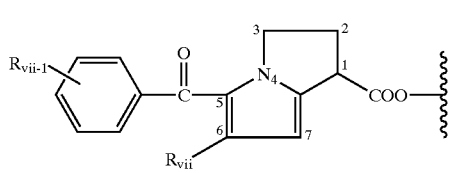

(IIC)

Group VE)

(XC)

(XI)

(XIII)

(XXXX)

(XXXXI)

In group V), the compounds have the following meanings:
when R is the formula (IIC),
$R_{vii}$ is H or a linear or branched when possible $C_1$–$C_4$ alkyl;
$R_{vii-1}$ is $R_{vii}$, or a linear or branched when possible $C_1$–$C_4$ alkoxy; Cl, F, Br; the position of $R_{vii-1}$ being ortho, or meta, or para;
the residue of the known Ketorolac is preferred, wherein $R_{vii}$ and $R_{vii-1}$ are H, and A=R (A being the group of the formula A—$X_1$—$NO_2$) and t=0;
when R is the formula (V),
of which the residue of the known tenidap has been mentioned, as described and obtained in U.S. Pat. No. 4,556,672 herein incorporated by reference;
in these compounds of formula (V) A=R and t=0,
when R is the formula (VIIC),
of which the residue of the known tenoxicam has been mentioned, A is RCO, t=1 u=0 or A is R and t=0, as described and obtained in DE 2,537,070 herein incorporated by reference;
when R is the formula (IXC),
wherein A=R and t=0, or A=RCO with t=1 and u=0, the residue of the known piroxicam has been indicated, as described and obtained in U.S. Pat. No. 3,591,584 herein incorporated by reference;
when R is the formula (IIIC),
wherein A=RCOO, t=1 and u=0 or 1; or t=0 and A=R, of which the residue of the known nabumetone has been indicated, as described and obtained in U.S. Pat. No. 4,061,779 herein incorporated by reference;
when R is the formula (IVC)
wherein A=RCOO, t=1 and u=1, of which the indomethacin residue has been indicated, as described and obtained in U.S. Pat. No. 3,161,654 herein incorporated by reference;
when R is the formula (XC), the residue X is known as meloxicam;
the preferred compounds are those wherein A=RCO, t=1 and u=0;
when R is the formula (XI) the residue is known as ampiroxicam
when the end group is —$CH(CH_3)OCOC_2H_5$; the preferred compounds have A=RCO, t=1 and u=0;
when R is the formula (XIII) and the valence is saturated with H
the residue derives from lornoxicam; the preferred compounds have A=RCO, t=1 and u=0;
when R is the formula (XXXX) and the valence is saturated with H
the compound known as paracetamol is obtained, as described and obtained in U.S. Pat. No. 2,998,450 herein incorporated by reference;
when R is the formula (XXXXI) and the valence is saturated with H
the compound known as Tramadol is obtained, as described and obtained in U.S. Pat. No. 3,652,589; the preferred compounds according to the present invention obtainable with the radicals corresponding to the formulas (XXXX) and (XXXXI) have A=RCO, t=1 and u=0.
Y in the above mentioned $X_1$ formula contains one or two nitrogen atoms in the ring, and preferably selected from the following:

(Y1)

(Y2)

(Y3)

-continued

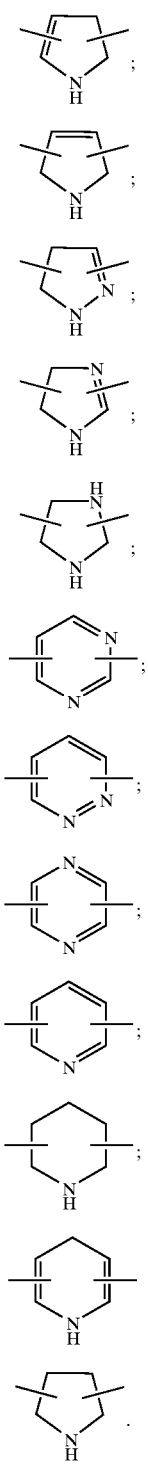

(Y4)
(Y5)
(Y6)
(Y7)
(Y8)
(Y9)
(Y10)
(Y11)
(Y12)
(Y13)
(Y14)
(Y15)

The preferred of Y is Y12 (pyridyl) substituted in position 2 and 6. The bonds can be also in non symmetric position, for example Y12 (pyridyl) can be substituted also in position 2 and 3; Y1 (pyrazol) may be 3,5-disubstituted.

The $X_1$ precursors, wherein the oxygen free valence is saturated with H and the free valence of the end carbon is saturated either with a carboxylic or hydroxyl group, are commercially available products or are obtainable with methods known in the prior art.

The compounds containing R of group I) of the type Ia) are described in the patent WO 92/01668 wherein the preparation methods are also described. This patent is herein incorporated by reference. The type Ib) compounds are for example prepared by using the method shown in The Merck Index, XI ed., 1989, pag. 16, No. 95 for the residue of the acetylsalicylsalicylic acid. The changes of the compounds of formula Ib) may be obtained by applying the processes mentioned in the patent WO 92/01668.

Compounds Ic) of the $Ic_1$) class, in which the radical is a 5-amino salicylic acid derivative (5-amino-2-hydroxybenzoic acid) known as mesalamine, when the starting radical contains —COOH, are prepared by reduction of the m-nitrobenzoic acid with Zn powder and HCl (see H. Weil et al., Ber. 55B, 2664 (1922)), or by electrolytic reduction: Le Guyader, Peltier, Compt. Rend. 253, 2544 (1961). These publications are herein incorporated by reference.

The starting radical $Ic_2$), when it contains —COOH, is known as olsalazine: 3,3'-azabis(6-hydroxybenzoic) acid; and it is prepared according to EP 36,636 or U.S. Pat. No. 4,528,367, both herein incorporated by reference.

The $Ic_3$) compounds are prepared according to U.S. Pat. No. 2,396,145 herein incorporated by reference.

Equivalent compounds to $Ic_1$), $Ic_2$) and $Ic_3$) contain the substituents mentioned in the above references.

The compounds wherein R is of the group II) are described in the patents WO 94/04484 and U.S. Pat. No. 3,558,690 wherein the preparation methods are also described. These patents are herein incorporated by reference.

The starting compound of IIb), when the valence is saturated with —COOH (flunixin), is obtained according to U.S. Pat. No. 3,337,570 and U.S. Pat. No. 3,689,653, both herein incorporated by reference. The compounds containing the substituents mentioned in the previous patents are equivalent to flunixin.

The compounds wherein R is of group III) are described and obtained with the processes mentioned in the following patents:

patent application PCT/EP/93 03193; for the compounds of formula (IV) see also U.S. Pat. No. 3,641,127; for the compounds of formula (XXI) see also U.S. Pat. No. 3,896,145; for the compounds of formula (IX) residue of flurbiprofen see also U.S. Pat. No. 3,755,427; for the compounds of formula (II) see also U.S. Pat. No. 4,035,376; for the compounds of formula (VI) see also U.S. Pat. No. 3,997,669; for the compounds of formula (VIII) see also U.S. Pat. No. 3,843,681; for the compounds of formula (VII) see also U.S. Pat. No. 3,600,437; for the compounds of formula (III) see also U.S. Pat. No. 3,784,701.

All the Above Mentioned Patents are Herein Incorporated by Reference.

The processes for preparing the compounds of class IIID) are the following:

The residue IIIa) is obtained by preparing the acid compound according to U.S. Pat. No. 3,931,205, the valence is saturated with —CH(CH$_3$)—COOH. The compounds containing the substituents mentioned in the above patent are equivalent to pranoprofen. The residue (XXX) is prepared through the compound with the —CH(CH$_3$)—COOH group (bermoprofen) according to U.S. Pat. No. 4,238,620 herein incorporated by reference. Other equivalent products are described in the above mentioned patent.

The residue (XXXI) is prepared starting from the corresponding —CH(CH$_3$)—COOH acid according to U.S. Pat. No. 4,254,274. Equivalent compounds are described in the same patent.

The residue (XXXII) is prepared according to EP 238,226 herein incorporated by reference, when the valence is saturated with —$CH_2$—COOH. Equivalent products are reported in said patents as substituted 1,3,4,9 tetrahydropyrane [3,4-b]indol-1-acetic acids.

The residue (XXXIII) is prepared from pirazolac and the valence is saturated with —$CH_2$—COOH, as mentioned in EP 54,812 herein incorporated by reference. Equivalent products are described in said patent.

The residue (XXXVI) is prepared according to UK 2,035, 311 herein incorporated by reference, starting from zaltoprofen and having the —CH($CH_3$)—COOH end group. Equivalent products are described in said patent.

The preparation process of the residue (XXXVII) is obtained starting from mofezolac and is prepared according to EP 26,928. Equivalents products are reported in the same patent.

The compounds in which R is of the group IV) are described in the British patent application 2,283,238, wherein also the preparation methods are indicated; this patent is herein incorporated by reference.

In the group IV) the compounds can also be obtained: for the compounds of formula (II) using U.S. Pat. No. 3,904, 682; the compounds of formula (X) according to U.S. Pat. No. 4,161,538, the compounds of formula (III) according to U.S. Pat. No. 3,228,831. These patents herein mentioned are here incorporated by reference.

In the group V) the compounds can also be obtained: for the compounds of formula (II) using U.S. Pat. No. 4,089,969 herein incorporated by reference; the compounds of formula (V) can be obtained according to U.S. Pat. No. 4,556,672 herein incorporated by reference.

The residue (X) is prepared according to the German patent 2,756,113. Equivalent products are described in said patent.

The residue (XI) is-prepared according to EP 147,177, starting from ampiroxicam having the —CH($CH_3$)OCO$OC_2H_5$ end group. Equivalent products are described in said patent.

The residue (XII) is prepared according to J. Med. Chem., vol. 27 n. 11, November 1984, Walsh et Al. "Antiinflammatory Agents. 3. Synthesis and Pharmacological Evaluation of 2-amino-3-benzoylphenylacetic Acid and Analogues". Equivalent products are described in said publication.

The residue (XIII) is prepared starting from lornoxicam, wherein the valence is saturated with H. It is prepared according to GE 2,003,877. Equivalent products are described in said patent.

Generally the connection between A and $X_1$ is, as seen, of ester or amidic type (NH or $NR_{1c}$, as defined in X) when R is of groups I, II, III, IV and V. All well known synthesis routes for forming such bonds may be used to form said connection.

In the case of esters of groups I, II, III and IV, and for the compounds of group V ending with a carboxylic function, the most direct synthetic route to obtain the corresponding nitroxyderivatives of the present invention involves:

a) reaction of the acyl chlorides R—CO—Cl with halogen alcohols of the HO—$X_{1Z}$—Cl, HO—$X_{1Z}$—Br, HO—$X_{1Z}$—I type, wherein $X_{1Z}$ is $X_1$ as above defined without the oxygen atom, in the experimental conditions of the prior art, and isolation of compounds of formula R—CO—O—$X_{1Z}$—Cl (Br, I). The above products can also be obtained by reaction of the sodium or potassium salts of said R—CO—OH acids with dihalogen derivatives of general formula $X_{1Z}Cl_2$, $X_{1Z}Br_2$ or $X_{1Z}I_2$.

b) The above products are transformed into the final products by reaction with $AgNO_3$ in acetonitrile, according to what known in the prior art.

The general schemes are the following:

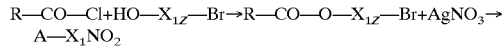

wherein $X_1$=$X_{1Z}$O.

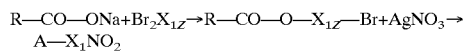

wherein $X_1$=$X_{1Z}$O.

In the case of amides the synthetic sequence involves the reaction of the same acyl chlorides RCOCl with aminoalcohols of general formula $NH_2$—$X_{1Z}$—OH, $NHR_{1C}$—$X_{1Z}$—OH to give amides of general formula:

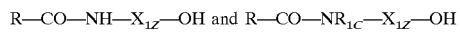

according to known methods.

The reaction of said amides with halogenating agents such as for example $PCl_5$, $PBr_3$, $SOCl_2$ etc. leads to halogen derivatives of general formula:

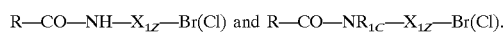

The latter by reaction with $AgNO_3$ in acetonitrile, according to known methods in the prior art, lead to the final products A—$X_1$—$NO_2$.

The synthesis scheme is the following:

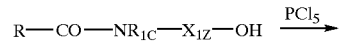

wherein $X_{1Z}$O is $X_1$.

c) An alternative route to the synthesis through steps a) and b) above is the reaction of the acid sodium or potassium salts with the nitric esters of halogenoalcohols of general formula:

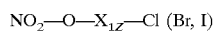

to give directly the nitroxy derivatives of the invention. The reaction scheme is the following:

wherein $X_{1Z}$O is $X_1$.

Synthetic routes similar to those above described are used for the products of group V, for example tenoxicam and piroxicam, wherein a dihalogen derivative of formula $Br_2X_{1Z}$ is reacted with the corresponding enolates. The products obtained are then transformed into the compounds of the invention by reaction with $AgNO_3$ in acetonitrile according to the above reported reaction scheme.

The scheme is herein reported for the piroxicam of formula IX of group V.

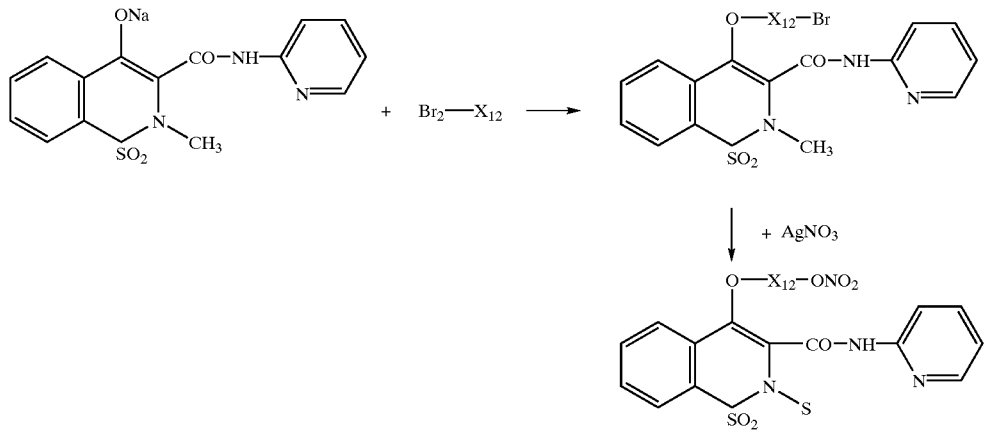

Group V products, such as tenoxicam and piroxicam, wherein the antiinflammatory reactive function is an hydroxyl, can be also reacted with an acyl chloride of formula ClCO—$X_{1Z}$—$Q_f$ wherein $Q_f$ is Cl, Br, I, OH. When $Q_f$=OH, the hydroxyl is substituted with an halogen as above described before the final nitration reaction with $AgNO_3$.

Nitration is carried out as above described.

In order to obtain the compounds of formula A—$X_1$—NO, acyl chlorides of formula R—COCl are reacted with HX—$X_{1Z}$—OH, wherein R, X and $X_{1Z}$ have the above mentioned meanings, in the experimental conditions described in the prior art. The obtained alcohols are reacted with sodium nitrite in a solvent, for instance constituted of a mixture of water with tetrahydrofuran in the presence of hydrochloric acid. The reaction is described in the prior art. The general scheme is the following:

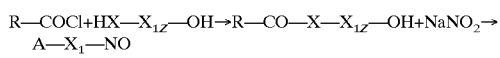

The compounds according to the present invention are transformed into the corresponding salts by reaction in organic solvent such as for example acetonitrile and tetrahydrofuran with an equimolecular amount of the corresponding organic or inorganic acid.

Examples of suitable organic acids are: oxalic, tartaric, maleic, succinic, citric acid.

Examples of suitable inorganic acids are: nitric, hydrochloric, sulphuric, phosphoric acid.

Another object of the invention is that it has surprisingly been found that the invention products containing ON—$(O)_Z$ groups are able to exert also an inhibiting effect of the inflammation induced by liposaccharide (LPS) and therefore are usable in septic shock.

This is surprising, since it is well known that generally antiinflammatories do not meaningfully change the nitrosynthetase activity induced by lipopolysaccharides in the rat and therefore they cannot be used in septic shock.

The compounds of the present invention can be used as antiinflammatory drugs or for the therapy and prophylaxis of cardiovascular diseases and of those pathologies wherein cellular hyperproliferation plays an important pathogenetic role.

It must be understood that when the compounds of the various groups contain at least one asymmetric carbon, the products can be used in racemic form or as single isomers. It is indeed well known that in the therapeutic uses of the invention generally an isomeric form is more active than the others. When the compounds present cis/transisomers, they can be used in this separated form or in admixture.

The pharmaceutical formulations of the compounds according to the present invention contain the same dose of the antiinflammatory precursor products, or lower.

The pharmaceutical formulations can be given by as or parenterally and can be prepared according to well known processes in the prior art. See the volume "Remington's Pharmaceutical Sciences".

The following Examples are given for illustrative purposes but are not limitative of the present invention.

EXAMPLE 1

Synthesis of 2-Acetyloxybenzoic Acid 6-(Nitroxymethyl)-2-pyridinylmethyl Ester Chlorhydrate (NCX 4050) of Formula (NCX 4050)

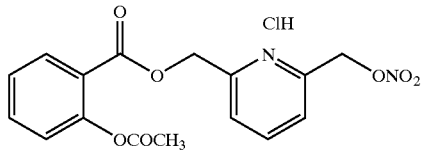

starting From the Acetylsalicylic Acid (Formula F1A) and 2,6-bis-(Hydroxymethyl)pyridine (Formula F1B)

(F1A)

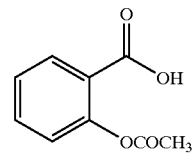

(F1B)

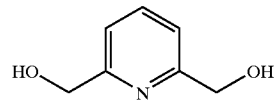

A) Synthesis of 2,6-bis-(Chloromethyl)pyridine

To thionyl chloride (11.6 ml, 158 mmoles), cooled at 0° C., 2,6-bis-(hydroxymethyl)pyridine (4 g, 28 mmoles) is very slowly added. The obtained solution is left under stirring for 2 hours at room temperature, then the thionyl chloride in excess is evaporated at reduced pressure. The obtained residue is treated with chloroform and evaporated again at reduced pressure to eliminate the thionyl chloride residues. The crude product is treated with chloroform and washed with water. The organic phase is anhydrified with sodium sulphate and dried obtaining 4.81 g of the product as white solid having m.p.=76°–78° C.

B) Synthesis of 2-Acetyloxybenzoic Acid 6-(Chloromethyl)-2-methylpyridinyl Ester To a solution of salicylic acid (1.6 g, 8.88 mmoles) in N,N'-dimethylformamide (20 ml) and under stirring sodium ethylate (0.64 g, 8.88 mmoles) is added. After 30 minutes the obtained solution is added to a solution of 2,6-bis-(chloromethyl)pyridine (4.72 g, 26.81 mmoles) in N,N'-dimethylformamide (20 ml). The solution is left at room temperature for 7 days, under stirring, then is diluted with ethyl ether and washed with water. The separated organic phases are anhydrified with sodium sulphate and the solvent is evaporated at reduced pressure. The reaction crude product is purified by chromatography on silica gel by eluting with n-hexane/ethyl acetate 7/3. 1.7 g of the product as yellow oil are obtained.

$^1$H-NMR (2.00 MHz) (CDCl$_3$): 8.10 (1H, d); 7.74 (1H, t); 7.57 (1H, t); 7.42 (1H, d); 7.33 (2H, m); 7.11 (1H, d); 5.42 (2H, s); 4.67 (2H, s); 2.41 (3H, s).

C) Synthesis of 2-Acetyloxybenzoic Acid 6-(Nitroxymethyl)-2-methylpyridinyl Ester To a solution of 2-acetyloxybenzoic acid 6-(chloromethyl)-2-methylpyridinyl ester (1.5 g, 4.7 mmoles) in acetonitrile (20 ml) maintained under stirring, silver nitrate is added (1.3 g, 7.65 mmoles). The solution is heated to 80° C., maintaining it sheltered from light, under stirring for 30 hours. The formed silver chloride is filtered, the solvent is evaporated. The reaction crude product is purified by silica gel chromatography by eluting with n-hexane/ethyl acetate 7/3. 1.2 g of product as yellow oil are obtained.

$^1$H-NMR (200 MHz) (CDCl$_3$): 8.10 (1H, d); 7.74 (1H, t); 7.57 (1H, t); 7.42 (1H, d); 7.33 (2H, m); 7.11 (1H, d); 5.60 (2H, s); 5.42 (2H, s); 2.41 (3H, s).

D) Synthesis of 2-Acetyloxybenzoic Acid 6-(Nitroxymethyl)-2-methylpyridinyl Ester Hydrochloride To a solution of 2-acetyloxybenzoic acid 6-(nitroxymethyl)-2-methylpyridinyl ester (1 g, 2.88 mmoles) in ethyl acetate (20 ml) cooled at 0° C., a solution of ethyl acetate/HCl 5M is added by dropping under stirring. It is left for one hour at 0° C., then the temperature is let reach room values. The formed precipitate is filtered and washed with ethyl ether. 900 mg of solid product are obtained.

Elementary analysis: Calculated: C, 50.21%; H, 3.95%; N, 7.31%; Cl, 9.26%. Found: C, 50.23%; H, 3.97%; N, 7.29%; Cl, 9.20%.

EXAMPLE 2

Synthesis of 2-Acetyloxybenzoic Acid 6-(Nitroxymethyl)-2-pyridinylmethyl Ester Nitrate (NCX 4051) of Formula

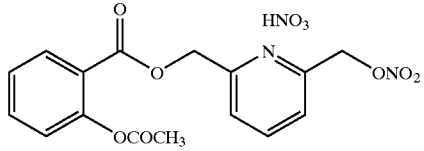

(NCX 4051)

starting from the 2-acetyloxybenzoic acid 6-(nitroxymethyl)-2-methylpyridinyl ester, isolated at step C) of the previous Example 1.

Synthesis of 2-Acetyloxybenzoic Acid 6-(Nitroxymethyl)-2-methylpyridinyl Ester Nitrate To a solution of 2-acetyloxybenzoic acid 6-(nitroxymethyl)-2-methylpyridinyl ester (1 g, 2.88 mmoles) in acetonitrile (10 ml) cooled at 0° C., a solution of 65% nitric acid (0.2 ml) in acetonitrile (2 ml) is added by dropping under stirring. It is left for 2 hours at 0° C., then the temperature is let reach room values. The formed precipitate is filtered and washed with ethyl ether. 1 g of solid product is obtained.

Elementary analysis: Calculated: C, 46.95%; H, 3.69%; N, 10.26%. Found: C, 46.99%; H, 3.72%; N, 10.22%.

EXAMPLE 3

Synthesis of the (S)-6-Methoxy-α-methylnaphthaleneacetic Acid 6-(Nitroxymethyl)-2-pyridinylmethyl Ester Hydrochloride of Formula

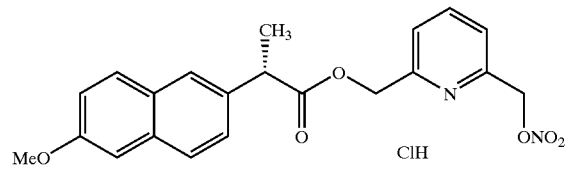

starting from naproxen (formula F3A) and 2,6-bis-(hydroxymethyl)pyridine (formula F1B)

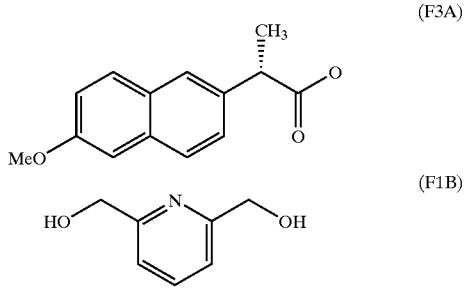

The compound is synthetized following the procedure repeorted in Example 1. Yield 38%.

Elementary analysis: Calculated: C, 58.25%; H, 4.88%; N, 6.47%; Cl, 8.19%. Found: C, 58.29%; H, 5.00%; N, 6.44%; Cl, 8.11%.

EXAMPLE 4

Synthesis of the (S)-6-Methoxy-α-methylnanthaleneacetic Acid 6-(Nitroxymethyl)-2-pyridinylmethyl Ester Nitrate of Formula 5

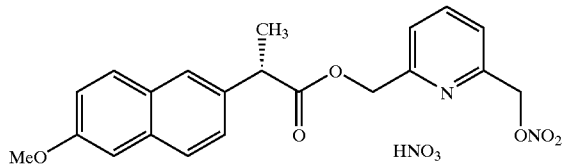

The compound is synthetized following the procedure reported in Example 2. Yield 42%.

Elementary analysis:

| | | | |
|---|---|---|---|
| Calculated | C 54.88% | H 4.60% | N 9.15% |
| Found | C 54.91% | H 4.65% | N 9.10% |

EXAMPLE 5

Synthesis of the 2-Fluoro-α-methyl-(1,1'biphenyl)-4-acetic Acid 6-(Nitroxymethyl)-2-pyridinylmethyl Ester Hydrochloride of Formula

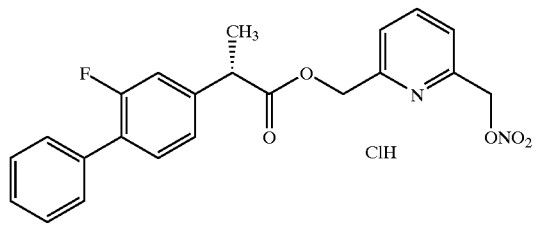

starting from flurbiprofen (formula F5A) and 2,6-bis-(hydroxymethyl)pyridine (formula F1B)

(F5A)

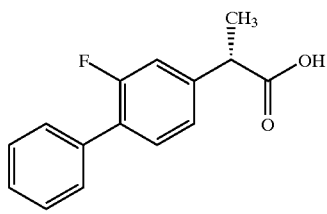

(F1B)

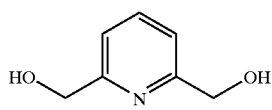

The compound is synthetized following the procedure reported in Example 1. Yield 35%.

Elementary analysis:

| | | | | | |
|---|---|---|---|---|---|
| Calculated | C 59.12% | H 4.51% | N 6.29% | Cl 7.93% | F 4.25% |
| Found | C 59.17% | H 4.55% | N 6.21% | Cl 7.91% | F 4.22% |

EXAMPLE 6

Synthesis of the 2-Fluoro-α-methyl-(1,1'biphenyl)-4-acetic Acid 6-(Nitroxymethyl)-2-pyridinylmethyl Ester Nitrate or Formula

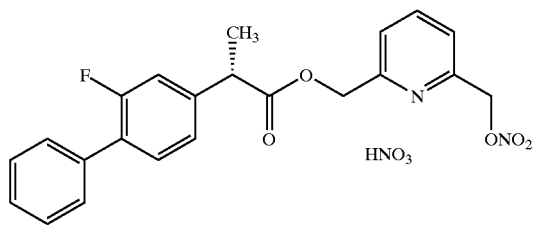

The compound is synthetized following the procedure reported in Example 2. Yield 39%.

Elementary analysis:

| | | | | |
|---|---|---|---|---|
| Calculated | C 55.79% | H 4.26% | N 8.91% | F 4.01% |
| Found | C 55.83% | H 4.30% | N 8.88% | F 4.00% |

EXAMPLE 7

Synthesis of the 1-(4-Chlorobenzoyl)-5-methoxy-2-methyl-1H-indol-3-acetic Acid 6-(Nitroxymethyl)-2-pyridinylmethyl Ester Hydrochloride of Formula

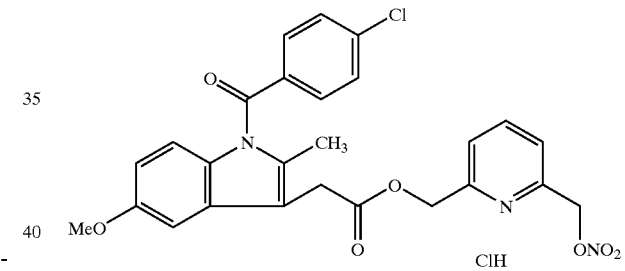

starting from indomethacin (formula F7A) and 2,6-bis-(hydroxymethyl)pyridine (formula F1B)

(F7A)

(F1B)

The compound is synthetized following the procedure reported in Example 1. Yield 41%.

Elementary analysis: Calculated: C, 55.71%; H, 4.13%; N, 7.53%; Cl, 12.65%. Found: C, 55.73%; H, 4.16%; N, 7.49%; Cl, 12.64%s.

EXAMPLE 8

Synthesis of 1-(4-Chlorobenzoyl)-5-methoxy-2-methyl-1H-indol-3-acetic Acid 6-(Nitroxymethyl)-2-pyridinylmethyl Ester Nitrate of Formula

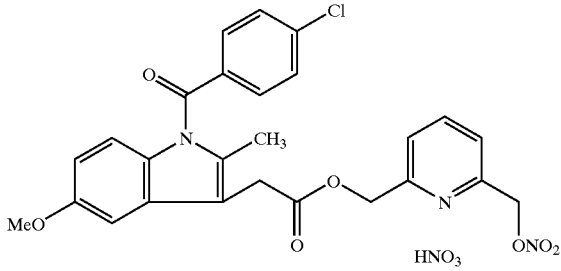

The compound is synthetized following the procedure reported in Example 2. Yield 35%.

Elementary analysis: Calculated: C, 53.18%; H, 3.95%; N, 9.58%; Cl, 6.04%. Found: C, 53.20%; H, 4.41%; N, 9.56%; Cl, 6.01%.

EXAMPLE 9

Comparative

Preparation of 1-(4-Chlorobenzoyl)-5-methoxy-2-methyl-1H-indol-3-acetic Acid 3-(Nitroxymethyl)phenyl Ester of Formula

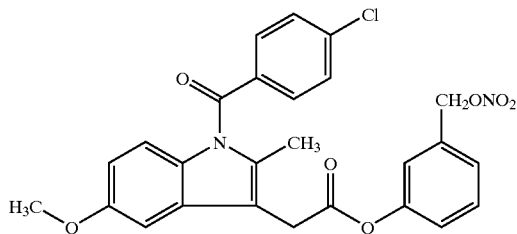

wherein the precursor drug is indomethacin (formula F7A).

a) Synthesis of 1-(4-Chlorobenzoyl)-5-methoxy-2-methyl-1H-indol-3-acetic Acid 3-(Formyl)phenyl Ester To a solution of 3-hydroxybenzaldehyde (g 8.30) and triethylamine (g 0.824) in methylene chloride (200 ml), cooling at a temperature in the range −5° C.–0° C. indomethacin in the form of the corresponding acylchloride (g 16.50) is added under stirring. It is still maintained under stirring for 15 minutes, then water (100 ml) is added and the phases are separated. The aqueous phase is recovered and extracted with methylene chloride (300 ml). The organic phases are joined together, washed with a 5% $Na_2CO_3$ solution, the organic phase is anhydrified with sodium sulphate obtaining the expected compound.

b) Synthesis of 1-(4-Chlorobenzoyl)-5-methoxy-2-methyl-1H-indol-3-acetic Acid 3-(Hydroxymethyl)phenyl Ester The compound isolated in the previous step (g 1.9) is dissolved in ethyl acetate (100 ml) in the presence of palladium 5% on carbon (g 0.290) with the 50% of humidity. The mixture is hydrogenated at room temperature and hydrogen pressure of about 2.5 atm, under stirring. After 12 hours the catalyst is removed by filtration under vacuun, washing with ethyl acetate (200 ml). The organic phases are joined together and washed with a 5% sodium bicarbonate solution and water. It is anhydrified with magnesium sulphate. It is filtered under vacuum and evaporated at reduced pressure obtaining the expected compound.

c) Synthesis of 1-(4-Chlorobenzoyl)-5-methoxy-2-methyl-1H-indol-3-acetic Acid 3-(Chloromethyl)phenyl Ester To a mixture formed by the compound isolated in the previous step (g 1.85) and thionyl chloride (ml 5.5), maintained under stirring, dimethylformamide (ml 0.5) is added at room temperature and left under stirring for one hour. At the end the thionyl chloride is evaporated at reduced pressure at a bath temperature lower than 40° C. The so obtained crude solid product is purified by crystallization with isopropyl ether (ml 30).

A solid is isolated which is dried under vacuum at room temperature, obtaining the expected compound.

d) Synthesis of the 1-(4-Chlorobenzoyl)-5-methoxy-2-methyl-1H-indol-3-acetic Acid 3-(Nitroxymethyl)phenyl Ester A solution of the compound isolated in the previous step (1.4 g) in acetonitrile (ml 8) is treated under stirring, sheltered from light and at room temperature with $AgNO_3$ (g 0.9). It is heated at ref lux for two hours and then cooled at room temperature and $AgNO_3$ (g 1.2) is added. It is filtered under vacuum, the precipitate (silver salts) is washed with acetonitrile. The organic phase is evaporated under vacuum at a bath temperature lower than 40° C. The obtained crude product is crystallized from isopropyl ether. The process global yield is 34%. By analyzing the final product by chromatography on thin layer of silica gel, using as eluent hexane/ethyl acetate 7/3, an unitary stain is obtained. m.p. 115–117° C. $^1$H-NMR ($CDCl_3$): 7.70 (2H, d), 7.49 (2H, d), 7.42 (1H, t), 7.14–7.06 (4H, m), 6.90 (1H, d), 6.70 (1H, dd), 5.42 (2H, s), 3.93 (2H, s), 3.86 (3H, s) 2.48 (3H, s).

EXAMPLE 10

Comparative

Synthesis of the 1-(4-Chlorobenzoyl)-5-methoxy-2-methyl-1H-indol-3-acetic Acid 4-Nitroxybutyl Ester To a solution of indomethacin (5.04 g, 14 mmoles) in chloroform (50 ml) at room temperature 1-chloro-4-butanol (1.4 ml, 14 mmoles), N,N' dicyclohexylcarbodiimide (2.87 g, 14 mmoles) and 4-dimethylaminopyridine (0.11 g, 0.09 mmoles) are added. The mixture is maintained under stirring at room temperature for 6 hours. The solid is filtered and the organic phase is washed with water, separated, dried with sodium sulphate and finally evaporated under vacuum. The obtained residue is purified by column chromatography (eluent n-hexane/ethyl acetate 9/1). An yellow-coloured oily residue (5.2 g), corresponding to 4-chlorobutyl ester of the indomethacin is isolated.

5 g of the compound (11 mmoles) are dissolved in acetonitrile (25 ml) and treated with silver nitrate (3.8 g, 22 mmoles). The mixture is let ref lux in the dark for 48 hours. After cooling, the solid residue is filtered and the solvent is evaporated under vacuum. The obtained residue is purified by column chromatography (eluent n-hexane/ethyl acetate 9/1). At the end an oil (4.2 g) is isolated.

$^1$H-NMR ($CDCl_3$, ppm): 7.65 (2H, m); 7.45 (2H, m); 6.95 (1H, d); 6.84 (1H, d); 6.66 (1H, dd); 4.10 (2H, t); 3.82 (3H, s); 3.65 (2H, s); 3.35 (2H, t); 2.39 (3H, s); 1.80 (4H, m).

EXAMPLE 11

Solubility Tests

Solubility tests in water of the salts of the 1-(4-chlorobenzoyl)-5-methoxy-2-methyl-1H-indol-3-acetic acid 6-(nitroxymethyl)-2-pyridinylmethyl ester (Ex. 7 and 8) by comparison with the 1-(4-chorobenzoyl)-5-methoxy-2-methyl-1H-indol-3-acetic acid 3-(nitroxymethyl)phenyl ester (Ex. 9) and with the 1-(4-chlorobenzoyl)-5-methoxy-2-methyl-1H-indol-3-acetic acid 4-nitroxybutyl ester have been carried out.

Said solubility tests have been effected by adding, at room temperature, in a 50 ml flask, 5 g of the substance and then bringing to volume with water.

The compounds according to the invention completely dissolve, therefore they show a solubility equal to at least 100 mg/ml.

The comparative compounds under the same conditions are unsoluble.

EXAMPLE 12

Example 11 has been repeated with the compounds from 1 to 6. All the compounds result soluble in water under the same conditions of the previous Example.

EXAMPLE 13

Synthesis of 2-[(2,6-Dichlorophenyl) aminobenzeneacetic Acid 6-(Nitroxymethyl)-2-pyridinylmethyl Ester Hydrochloride of Formula

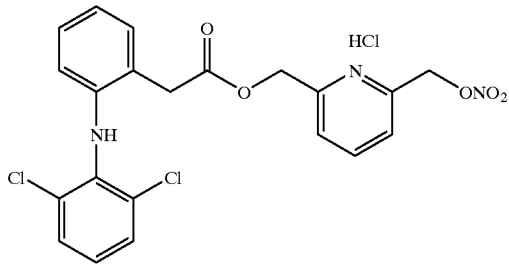

Starting From 2-[(2,6-Dichlorophenyl)aminobenzeneacetic Acid Sodium Salt (Formula) and 2,6-bis-(Hydroxymethyl) pyridine (F9A)

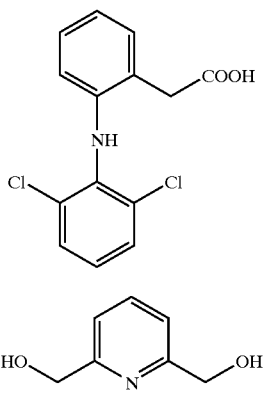

(F1B)

A) Synthesis of 2-[(2,6-Dichlorophenyl)aminobenzene Acetic Acid 6-(Chloromethyl)-2-methylpyridinil Ester To a solution of 2,6-bis-(chloromethyl)pyridine (3.83 g, 21.75 mmoles), prepared as described in Example 1A, in N,N'-dimethyl formamide (20 ml), under stirring, a solution of 2-[(2,6-dichloro phenyl)amino]benzene acetic acid sodium salt (3.04 g, 9.54 mmoles) in N,N'-dimethylformamide (25 ml) is added dropwise. The solution is stirred at room temperature for one day, then it is diluted with ethyl acetate and washed with water. The organic phases are recovered and anhydrified with sodium sulphate. The solvent is then evaporated under a reduced pressure. The crude reaction product is purified by chromatography on a silica gel column, eluted with n-hexane/ethyl acetate 8/2. 2.88 g of the product are obtained as a white solid. Yield 69%

$^1$H NMR (200 MHz) (CDCl$_3$): 7.66 (1H, t); 7.41 (1H, d); 7.33 (1H, d); 7.27 (1H, d); 7.18 (2H, m); 6.97 (2H, dd); 6.81 (1H, s); 6.57 (1H, d); 5.3 (2H, s); 4.62 (2H, s); 3.93 (2H, s).

B) Synthesis of 2-[(2,6-Dichlorophenyl)aminobenzene Acetic Acid 6-(Nitroxymethyl)-2-methylpyridinyl Ester To a stirred solution of 2-[(2,6-dichlorophenyl) aminobenzene acetic acid 6-(chloromethyl)-2-methylpyridinil ester (2.438 g, 5.59 mmoles) in 90 ml of acetonitrile is added silver nitrate (2.19 g, 12.89 mmoles). The solution is further stirred for 30 hours at 80° C. maintaining it sheltered from light. The formed silver chloride is filtered and the solvent evaporated. The crude reaction product is purified by silica gel column chromatography, eluted with n-hexane/ethyl acetate 7/3. 1.2 g of the product in the form of a yellow oil are obtained. Yield 46%.

$^1$H NMR (200 MHz) (CDCl$_3$): 7.69 (1H, dd); 7.33 (1H, d); 7.25 (1H, m); 7.23 (2H, m); 7.16 (1H, dd); 6.98 (2H, m); 6.82 (1H, s); 6.57 (1H, d); 5.49 (2H, s); 5.31 (2H, s); 3.94 (2H, s).

C) Synthesis of 2-[(2,6-Dichlorophenyl)aminobenzene Acetic Acid 6-(Nitroxymethyl)-2-methylpyridinyl Ester Hydrochloride To a solution of 2-[(2,6-dichlorophenyl)aminobenzene acetic acid 6-(nitroxymethyl)-2-methylpyridinil ester (0.400 g, 0.86 mmoles) in ethyl acetate (6 ml), cooled at 0° C., a solution of HCl/ethyl acetate 3M (0.6 ml) is added dropwise under stirring the reaction mixture is stirred for one hour at 0° C., then is warmed up to room temperature.

The formed precipitate is filtered and washed with ethyl ether. 0,310 g of solid product are obtained. Yield 73%.

Elementary analysis: Calculated: C, 50.58%; H, 3.63%; N, 8.42%; Cl, 21.32%. Found: C, 50.62%; H, 3.66%; N, 8.40%; Cl, 21.02%.

EXAMPLE 14

Synthesis of 2-[(2,6-Dichlorophenyl)aminobenzene Acetic Acid 6-(Nitroxymethyl)-2-methylpyridinyl Ester Nitrate of Formula

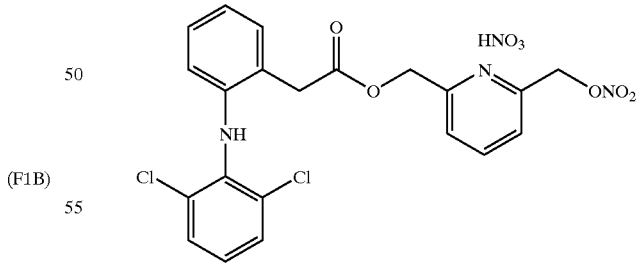

starting from 2-[(2,6-dichlorophenyl)aminobenzene acetic acid 6-(nitroxymethyl)-2-methylpyridinil ester, obtained in step B) of the previous example 13.

Synthesis of 2-[(2,6-Dichlorophenyl)aminobenzene Acetic Acid 6-(Nitroxymethyl)-2-methylpyridinyl Ester Nitrate To a solution of 2-[(2,6-dichlorophenyl)aminobenzene acetic acid 6-(nitroxymethyl)-2-methylpyridinil ester (0.760 g, 1.65 mmoles) in acetonitrile (6 ml), cooled at 0° C., a solution of nitric acid (65%) (0.150 ml) in acetonitrile (2 ml) is added dropwise, under stirring. The reaction mixture is stirred one hour at 0° C., then is warmed up to room temperature. The formed precipitate is filtered and washed with ethyl ether. 0,600 g of the product, in the form of a solid, are obtained. Yield 70%.

Elementary analysis:

| Calculated: | C 48.02% | H 3.45% | N 10.67% | Cl 13.50% |
| Found: | C 48.06% | H 3.47% | N 10.66% | Cl 13.60% |

EXAMPLE 15

Study of the Inhibition Effect on Smooth Muscle Contraction and Smooth Muscle Cell Proliferation As known, contraction and/or cell proliferation of smooth muscle are important steps in the inflammation process.

Smooth Muscle Contraction

New Zealand White Rabbits (2.0–2.5 kg) were killed by cervical dislocation, cavernosal tissue (corpus canvernosus) and aorta excised.

The tissue was mounted in organ baths for recording of isometric tension, according to the method described by Khan MA et al (BJU Int. 1999 84(6):720–4). Tissues were pre-contracted with phenylephrine (10 μM) and relaxation responses to carbachol assessed in the presence of the compound to be tested.

The compound of the invention used in the assay was 2-acetyloxybenzoic acid 6-(nitroxymethyl)-2-pyridinylmethyl ester hydrochloride (NCX 4050), which synthesis is described in preceding example 1.

The reference compound was 2-acetoxybenzoic acid (3-nitroxymethyl)phenyl ester of formula

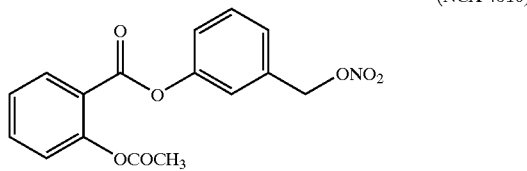

(NCX 4016)

which synthesis is described in ex. 3 of the PCT patent application WO 97/16405 filed in the Applicant's name.

Results are given in following Table 1, that showsthat the compound of the invention is more active than the reference compound in inhibiting smooth muscle contraction.

Smooth Muscle Cell Proliferation

Human saphenous veins were cultured by standard explant methods (J. Cardiovasc., Pharmacol. 1999, 33(2), 204–11). Tissues were collected into sterile pots containing PBS, penicillin and streptomycin. Under sterile tissue culture conditions, tissues were cut into small pieces (approximately 1 mg weight) and placed into a standard culture medium containing 20% fetal calf serum (FCS) for several days (medium changed every 2–4 days). $^3$H-thymidine was measured in the DNA fraction of cells cultured into 48 well plates. Cells were cultured to confluence in the medium containing 10% FCS. Cells were deprived of serum for 24 h before the addition of 10% FCS, together with different concentration of steroids. After 24 h, $^3$H-thymidine was added to the cells for 4 h. Cells were washed with phosphate buffered saline and ethanol. DNA was extracted with sodium hydroxide solution and the $^3$H material counted by scintillation. The data represents observations made in triplicate wells.

Table 2 reports results obtained on the inhibitory effect of the tested compounds on human vascular smooth cell proliferation.

The Table shows that the compound of the invention is much more active than the reference compounds.

Table 1 and 2 demonstrate that the antiinflammatory activity of the compound of the invention is higher than that of the reference compound.

TABLE 1

Inhibition of aorta and corpus cavernosum smooth muscle contraction at different concentrations ($10^{-4}$ and $10^{-5}$ M) of the compound of the invention (NCX 4050) and of the reference compound (NCX 4016)

| sample | concentration (log M) | % inhibition rabbit aorta | % inhibition rabbit corpus cav |
|---|---|---|---|
| NCX 4050 | −4 | 87 | 85 |
|  | −5 | 80 | 63 |
| NCX 4016 (comp.) | −4 | 20 | 47 |
|  | −5 | 18 | 14 |

TABLE 2

Inhibition of smooth muscle cell proliferation at different concentrations ($10^{-4}$ and $10^{-5}$ M) of the compound of the invention (NCX 4050) and of the reference compound (NCX 4016)

| sample | concentration (log M) | % inhibition cell proliferation |
|---|---|---|
| NCX 4050 | −4 | 95 |
|  | −5 | 82 |
| NCX 4016 (comp.) | −4 | 60 |
|  | −5 | 43 |

What is claimed is:

1. A compound of formula $$A-X_1-N(O)_z$$

or an organic or inorganic salt thereof, wherein:

z is 1 or 2;

A=R(COX$_u$)$_t$ and wherein t is 0 or 1; u is 0 or 1;

X=O, NH, NR$_{1c}$ wherein R$_{1c}$ is a linear or branched C$_1$–C$_{10}$ alkyl;

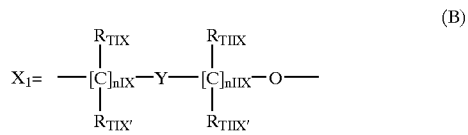

(B)

wherein:

nIX is an integer between 0 and 3;

nIIX is an integer between 1 and 3;

R$_{TIX}$, R$_{TIX'}$, R$_{TIIX}$, R$_{TIIX'}$, equal to or different from each other, are H or a linear or branched C$_1$–C$_4$ alkyl;

Y is a heterocyclic ring containing at least one salifiable nitrogen atom;

R is selected from the groups consisting of:

group 1) wherein t=1 and u=1

Ia)

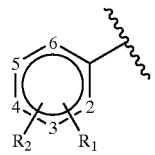

Ib)

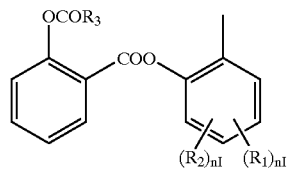

Ic)

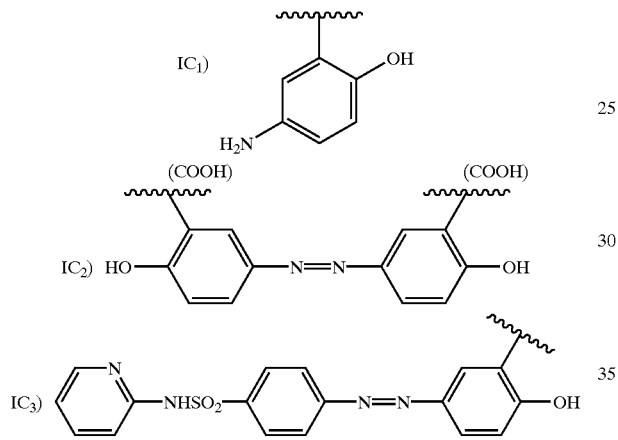

wherein:
- $R_1$ is an $OCOR_3$ group; $R_3$ is linear or branched $C_1$–$C_5$ alkyl, or the residue of a heterocycle with a single ring having 5 or 6 atoms which is aromatic, partially or totally hydrogenated, containing one or more hetero-atoms independently selected from O, N and S;
- $R_2$ is hydrogen, hydroxyl, halogen, a linear or branched $C_1$–$C_4$ alkyl, a linear or branched $C_1$–$C_4$ alkoxyl, a linear or branched $C_1$–$C_4$ perfluoroalkyl, nitro, amino, mono- or di-($C_{2-4}$) alkylamino;
- nI is 0 or 1;

group II) wherein t=1, u=1

IIa)

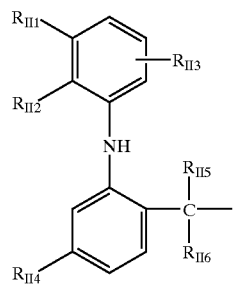

IIb)

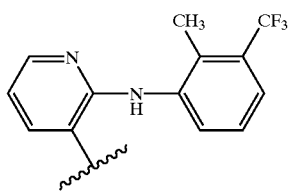

wherein
- $R_{II5}$ is H, a linear or branched $C_1$–$C_3$ alkyl;
- $R_{II6}$ has the same meaning as $R_{II5}$, or when $R_{II5}$ is H $R_{II6}$ may also be benzyl;
- $R_{II1}$, $R_{II2}$ and $R_{II3}$ are each independently hydrogen, a linear or branched $C_1$–$C_6$ alkyl a linear or branched $C_1$–$C_6$ alkoxy, or Cl, F, Br;
- $R_{II4}$ is $R_{II1}$ or bromine;

group III) wherein t=1, u=1

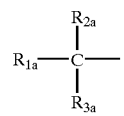

wherein:
- $R_{2a}$ and $R_{3a}$ are H, a linear or branched, substituted or non-substituted, $C_1$–$C_{12}$ alkyl or allyl, with the proviso that when one of $R_{2a}$ and $R_{3a}$ is allyl, the other is H;
- $R_{1a}$ is selected from the group consisting of:

(II)

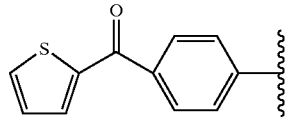

(XXI)

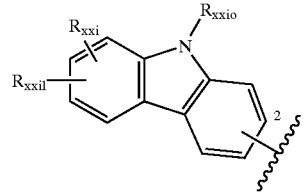

(IV)

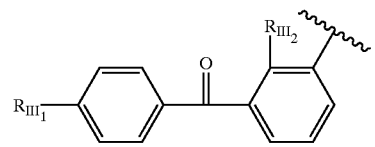

(XXXV)

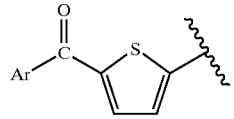

(VI)

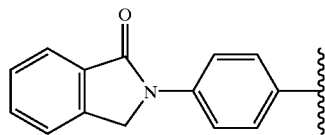

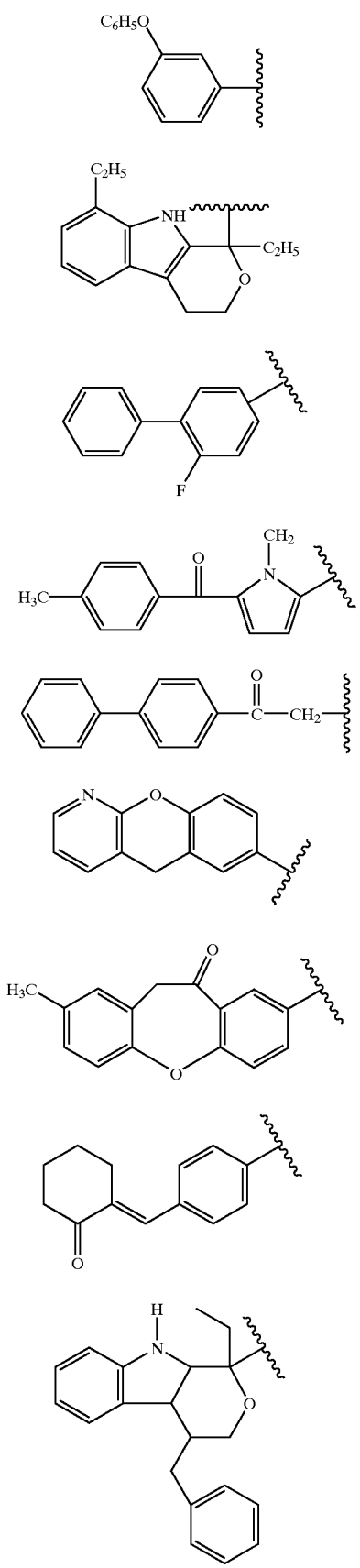
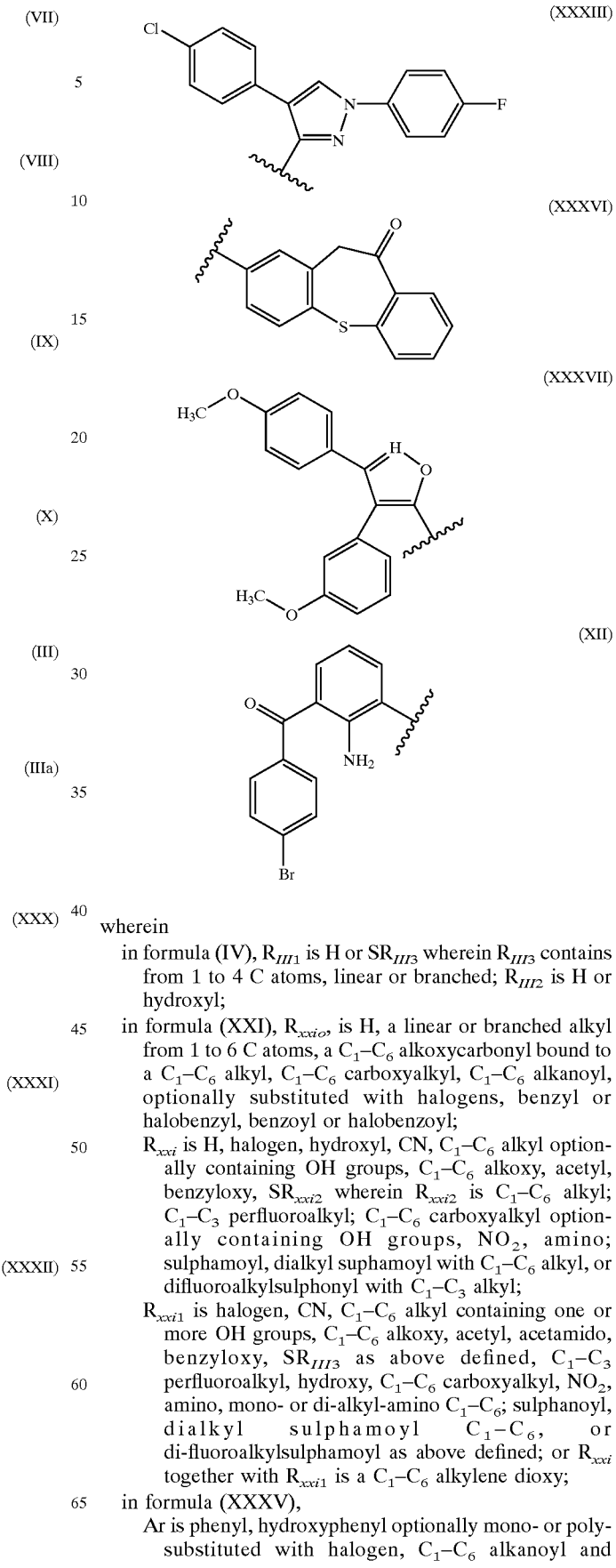

wherein
in formula (IV), $R_{III1}$ is H or $SR_{III3}$ wherein $R_{III3}$ contains from 1 to 4 C atoms, linear or branched; $R_{III2}$ is H or hydroxyl;

in formula (XXI), $R_{xxio}$, is H, a linear or branched alkyl from 1 to 6 C atoms, a $C_1$–$C_6$ alkoxycarbonyl bound to a $C_1$–$C_6$ alkyl, $C_1$–$C_6$ carboxyalkyl, $C_1$–$C_6$ alkanoyl, optionally substituted with halogens, benzyl or halobenzyl, benzoyl or halobenzoyl;

$R_{xxi}$ is H, halogen, hydroxyl, CN, $C_1$–$C_6$ alkyl optionally containing OH groups, $C_1$–$C_6$ alkoxy, acetyl, benzyloxy, $SR_{xxi2}$ wherein $R_{xxi2}$ is $C_1$–$C_6$ alkyl; $C_1$–$C_3$ perfluoroalkyl; $C_1$–$C_6$ carboxyalkyl optionally containing OH groups, $NO_2$, amino; sulphamoyl, dialkyl suphamoyl with $C_1$–$C_6$ alkyl, or difluoroalkylsulphonyl with $C_1$–$C_3$ alkyl;

$R_{xxi1}$ is halogen, CN, $C_1$–$C_6$ alkyl containing one or more OH groups, $C_1$–$C_6$ alkoxy, acetyl, acetamido, benzyloxy, $SR_{III3}$ as above defined, $C_1$–$C_3$ perfluoroalkyl, hydroxy, $C_1$–$C_6$ carboxyalkyl, $NO_2$, amino, mono- or di-alkyl-amino $C_1$–$C_6$; sulphanoyl, dialkyl sulphamoyl $C_1$–$C_6$, or di-fluoroalkylsulphamoyl as above defined; or $R_{xxi}$ together with $R_{xxi1}$ is a $C_1$–$C_6$ alkylene dioxy;

in formula (XXXV),
Ar is phenyl, hydroxyphenyl optionally mono- or poly-substituted with halogen, $C_1$–$C_6$ alkanoyl and alkoxy, $C_1$–$C_6$ trialkyl, cyclopentyl, cyclohexyl cycloheptyl, heteroaryl, furyl optionally containing OH, pyridyl;

group IV) wherein t=1, u=1

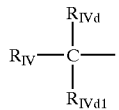

wherein:
one of $R_{IVd}$ and $R_{IVd1}$ is H and the other is H, a linear or branched alkyl from $C_1$ to $C_6$, difluoroalkyl with the alkyl having from 1 to 6 C atoms, or $R_{IVd}$ and $R_{IVd1}$ form together a methylene group;

$R_{IV}$ is selected from the group consisting of:

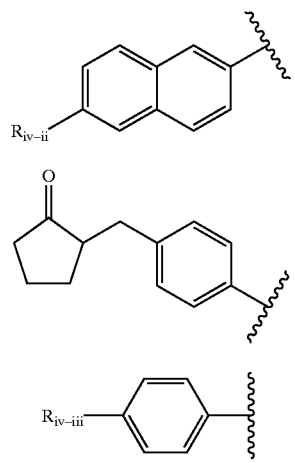

wherein:
in formula (II), $R_{iv-ii}$ is $C_1$–$C_6$ alkyl, $C_3$–$C_7$ cycloalkyl, $C_1$–$C_7$ alkoxymethyl, $C_1$–$C_3$ trifluoroalkyl, vinyl, ethynyl, halogen, $C_1$–$C_6$ alkoxy, difluoroalkoxy with the $C_1$–$C_7$ alkyl, $C_1$–$C_7$ alkoxymethyloxy, alkylthiomethyloxy with the $C_1$–$C_7$ alkyl, alkyl methylthio with the $C_1$–$C_7$ alkyl, cyano, difluoromethylthio, phenyl- or phenylalkyl substituted with the $C_1$–$C_8$ alkyl; in formula (III), $R_{iv-iii}$ is a $C_2$–$C_5$ alkyl, optionally branched, $C_2$ and $C_3$ alkyloxy, allyloxy, phenoxy, phenylthio, cycloalkyl having from 5 to 7 C atoms, optionally substituted in position 1 with a $C_1$–$C_2$ alkyl;

group V)

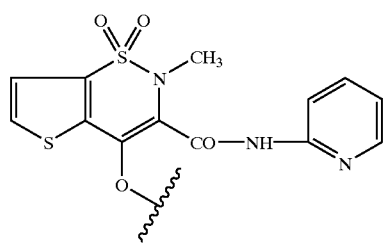

-continued

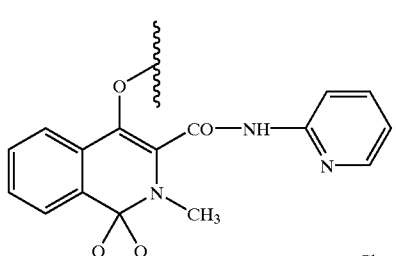

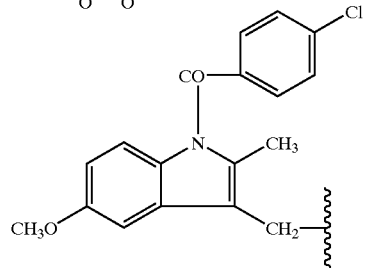

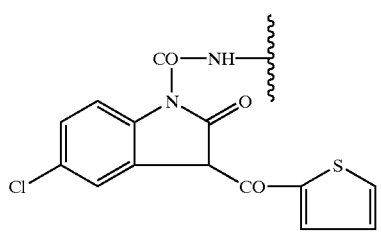

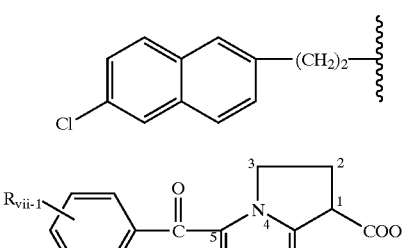

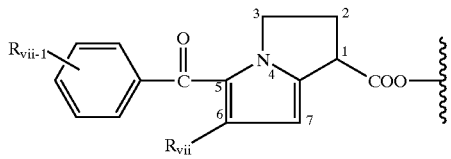

group VE)

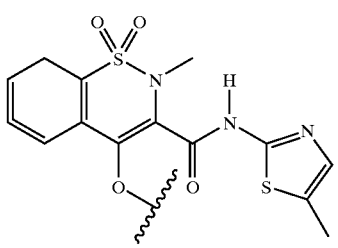

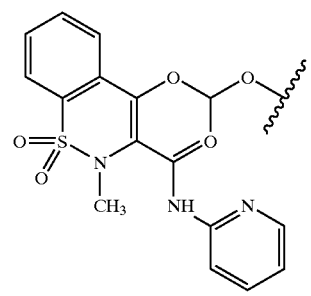

-continued

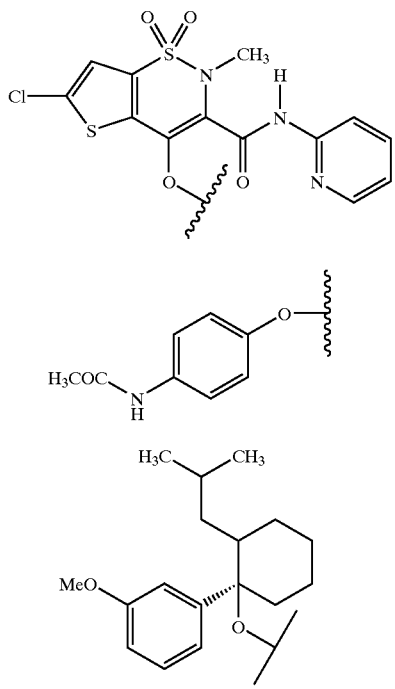

wherein in group V)
in formula (II), $R_{vii}$ is H or a linear or branched $C_1$–$C_4$ alkyl; $R_{vii-1}$ is $R_{vii}$ or a linear or branched $C_1$–$C_4$ alkoxy; Cl, F, Br; the position of $R_{vii-1}$ being ortho, or meta, or para;
when R is formula (V), A=R and t=0;
when R is formula (VII), A is RCO, and t=1 u=0 or t=0;
when R is formula (IX), A—R and t=0, or t=1 and u=0;
when R is formula (III), A=RCOO, t=1 and u=0 or 1; or t=0;
when R is formula (IV), A=RCOO, t=1 and u=1.

2. The compound, organic or inorganic salt according to claim 1, wherein in the compounds of formula A—$X_1$—N(O)$_z$ z is 2 and nIX and nIIX in the formula (B) of $X_1$ are integers equal to 1 and $R_{TIX}$, $R_{TIX'}$, $R_{TIIX}$, $R_{TIIX'}$ are equal to H.

3. The compound, organic or inorganic salt according to claim 1, wherein in the compounds of formula A—$X_1$—N(O)$_z$ R, X, u and t of the formula A=R(COX$_u$)$_t$, and Y in formula (B) of $X_1$, have the following meanings:
when R is selected from Group I),
in the compounds of formula Ia) X is equal to O or NH, $R_1$ is acetoxy, $R_2$ is hydrogen; in $X_1$ $R_{TIX}$=$R_{TIX'}$=$R_{TIIX}$=$R_{TIIX'}$=H, $n_{IX}$=1 and Y is an aromatic ring having 6 atoms, containing a nitrogen atom, said aromatic ring having the two free valences in position 2 and 6;
in the compounds of formula Ib) $R_3$=$CH_3$, nI=0, X is equal to O, $X_1$ is as above defined for Ia);
in the compounds of formula 1c) X=O and u=1;
when R is selected from group II),
in the formula IIa $R_{II1}$, $R_{II4}$ are hydrogen and $R_{II2}$ and $R_{II3}$ are chlorine in ortho-position with respect to NH; $R_{II5}$ and $R_{II6}$ are H, X is equal to O, and $X_1$ is as above defined for the compounds of formula Ia);

when R is selected from group III),
when $R_{1a}$ is as defined in formula (IV), $R_{III1}$, and $R_{III2}$ are H, $R_{3a}$ is H, and $R_{2a}$ is methyl, X=O;
when $R_{1a}$ is as defined in formula (XXI), $R_{xxio}$ is H, the linking bridge is in position 2, $R_{xxi}$ is H, $R_{xxi1}$ is chlorine and is in para position with respect to nitrogen;
when $R_{1a}$ is as defined in the formula (XXXV), Ar is phenyl, $R_{3a}$ is H, $R_{2a}$ is methyl and X is O;
when $R_{1a}$ is as defined in the formula IIIa), $R_{2a}$=H, $R_{3a}$=$CH_3$, u=1 and X=O;
when $R_{1a}$ is as defined in the formula (XXX), $R_{2a}$=H, $R_{3a}$=$CH_3$, u=1 and X=O;
when $R_{1a}$ is as defined in the formula (XXXI), $R_{2a}$=H $R_{3a}$=$CH_3$, u=1 and X=O;
when $R_{1a}$ is as defined in the formula (XXXII), $R_{2a}$=$R_{3a}$=H, u=1 and X=O;
when $R_{1a}$ is as defined in the formula (XXXIII), $R_{2a}$=$R_{3a}$=H, u=1 and X=O,
when $R_{1a}$ is as defined in the formula (XXXVI), $R_{2a}$=H, $R_{3a}$=$CH_3$, u=1 and X=O;
when $R_{1a}$ is as defined in the formula (XXXVII), $R_{2a}$=$R_{3a}$=H, t=1 and X=O;
when $R_{1a}$ is as defined in the formula (XII), $R_{2a}$=$R_{3a}$=H, u=1, t=1, X=O; or t=O;
when R is selected from group IV),
when $R_{IV}$ is the formula (II), $R_{iv-ii}$=$CH_3$O—, $R_{IVd}$=H and $R_{IVd1}$=$CH_3$, X=O and $X_1$ is as above defined for the compounds of formula Ia);
when $R_{IV}$ is the formula (X), $R_{IVd}$=H, $R_{IVd1}$=$CH_3$, X=O and $X_1$ is as above defined for Ia);
when $R_{IV}$ is the formula (III), $R_{iv-iii}$ is

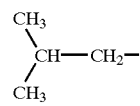

and $R_{IVd}$=H, $R_{IVd1}$ is $CH_3$, X=O and $X_1$ is as above defined for the compounds of formula Ia);
when R is selected from group V,
when R is the formula (II), $R_{vii}$ and $R_{vii-1}$ are H, and A=R;
when R is the formula (X), A=RCO, t=1 and u=0;
when R is the formula (XI), A=RCO, t=1 and u=0;
when R is the formula (XIII), A=RCO, t=1 and u=0;
when R corresponds to the formula (XXXX) or (XXXXI), A=RCO, t=1 and u=0.

4. The compound, organic or inorganic salt according to claim 1, wherein Y in formula (B) of $X_1$ contains one or two nitrogen atoms in the ring and is selected from the following:

(Y1)

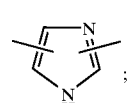

(Y2)

-continued (Y3) 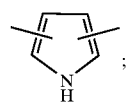

(Y4) 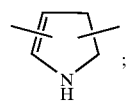

(Y5) 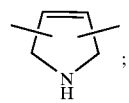

(Y6) 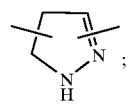

(Y7) 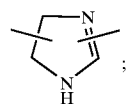

(Y8) 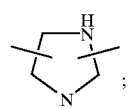

(Y9) 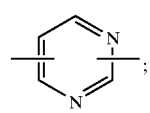

(Y10) 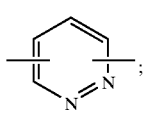

(Y11) 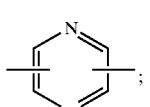

(Y12) 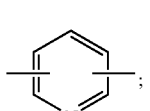

-continued (Y13) 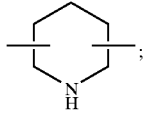

(Y14) 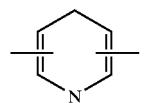

(Y15) 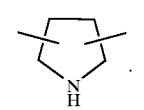

5. The compound, organic or inorganic salt according to claim 4, wherein the radical Y of formula (B) of $X_1$ is Y12 substituted in position 2 and 6.

6. The compound, organic or inorganic salt according to claim 1, wherein the organic acids are selected from the group consisting of: oxalic, tartaric, maleic, succinic, citric acids and the inorganic acids from nitric, hydrochloric, sulphoric, phosphoric acids.

7. The compound, organic or inorganic salt according to claim 1, wherein R in formula A=R $(COX_u)_t$ is selected from those of group I) and group IV).

8. A method for the treatment of inflammation, said method comprising administration an anti-inflammatory effective amount of a compound, organic or inorganic salt of claim 1.

9. A method for anti-thrombotic treatment said method comprising administration to a patient in need thereof an anti-thrombotic effective amount of a compound, organic or inorganic salt of claim 1.

10. A method for analgesic treatment of inflammation, said method comprising administration to a patient in need thereof an analgesic effective amount of a compound, organic or inorganic salt of claim 1.

11. A method for the treatment of septic shock said method comprising administration to a patient in need thereof an effective amount of a compound, organic or inorganic salt of claim 1.

12. Pharmaceutical formulations for oral and parenteral use containing as active principles the compound, organic or inorganic salt of claim 1.

* * * * *

UNITED STATES PATENT AND TRADEMARK OFFICE
CERTIFICATE OF CORRECTION

PATENT NO. : 6,613,784 B1
DATED : September 2, 2003
INVENTOR(S) : Francesca Benedini et al.

It is certified that error appears in the above-identified patent and that said Letters Patent is hereby corrected as shown below:

Column 3,
Line 25, delete "OCOR" and substitute therefor -- $OCOR_3$ --.

Column 8,
Line 57, delete "$R_{3a}$ = CH" and substitute therefor -- $R_{3a} = CH_3$ --.

Column 9,
Line 22, delete "(XB)" and substitute therefor -- (X) --.
Line 29, delete "(IIIB)" and substitute therefor -- (III) --.
Line 39, delete "(IIB)" and substitute therefor -- (II) --.
Line 48, delete "(X B)" and substitute therefor -- (X) --.
Line 53, delete "(IIIB)" and substitute therefor -- (III) --.

Column 10,
Line 4, delete "(VIIC)" and substitute therefor -- (VII) --.
Line 15, delete "(IXC)" and substitute therefor -- (IX) --.
Line 38, delete "(IVC)" and substitute therefor -- (IV) --.
Line 52, delete "(IIIC)" and substitute therefor -- (III) --.
Line 61, delete "(IIC)" and substitute therefor -- (II) --.

Column 11,
Line 3, delete "(XC)" and substitute therefor -- (X) --.
Line 53, delete "(IIC)" and substitute therefor -- (II) --.

Column 12,
Line 1, delete "(VIIC)" and substitute therefor -- (VII) --.
Line 7, delete "(IXC)" and substitute therefor -- (IX) --.
Line 12, delete "(IIIC)" and substitute therefor -- (III) --.
Line 18, delete "(IVC)" and substitute therefor -- (IV) --.
Line 23, delete "(XC)" and substitute therefor -- (X) --.

UNITED STATES PATENT AND TRADEMARK OFFICE
CERTIFICATE OF CORRECTION

PATENT NO.   : 6,613,784 B1
DATED        : September 2, 2003
INVENTOR(S)  : Francesca Benedini et al.

It is certified that error appears in the above-identified patent and that said Letters Patent is hereby corrected as shown below:

Column 20,
Line 55, delete the formula

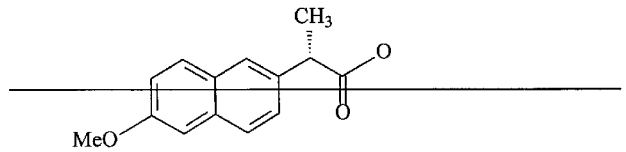

and substitute therefor the following formula

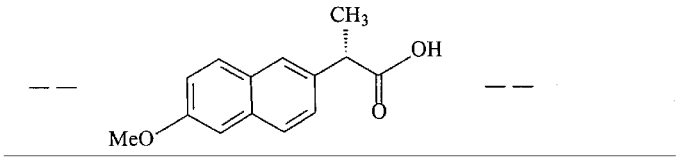

Column 28,
Line 2, delete "steroids" and substitute therefor -- compounds --.

Signed and Sealed this

Twentieth Day of July, 2004

JON W. DUDAS
*Acting Director of the United States Patent and Trademark Office*